(12) United States Patent
Brunelle et al.

(10) Patent No.: US 11,554,197 B2
(45) Date of Patent: Jan. 17, 2023

(54) DEVICE WITH AN OPEN CELL ELEMENT

(71) Applicant: BioMark, LLC, Reno, NV (US)

(72) Inventors: John Eric Brunelle, Reno, NV (US); Daniel Henry James, Jr., Alpharetta, GA (US)

(73) Assignee: BioMark, LLC, Reno, NV (US)

( * ) Notice: Subject to any disclaimer, the term of this patent is extended or adjusted under 35 U.S.C. 154(b) by 45 days.

(21) Appl. No.: 16/689,763

(22) Filed: Nov. 20, 2019

(65) Prior Publication Data
US 2020/0155728 A1 May 21, 2020

Related U.S. Application Data

(60) Provisional application No. 62/769,662, filed on Nov. 20, 2018.

(51) Int. Cl.
| | |
|---|---|
| *A61B 17/16* | (2006.01) |
| *A61L 31/14* | (2006.01) |
| *A61B 17/32* | (2006.01) |
| *A61B 17/02* | (2006.01) |
| *A61B 17/06* | (2006.01) |
| *A61L 31/02* | (2006.01) |
| *A61B 17/34* | (2006.01) |
| *A61L 31/16* | (2006.01) |
| *A61L 31/00* | (2006.01) |
| *A61B 17/3207* | (2006.01) |
| *A61B 17/3201* | (2006.01) |
| *A61B 17/3211* | (2006.01) |

(52) U.S. Cl.
CPC ............ *A61L 31/146* (2013.01); *A61B 17/02* (2013.01); *A61B 17/06066* (2013.01); *A61B 17/1604* (2013.01); *A61B 17/1615* (2013.01); *A61B 17/1655* (2013.01); *A61B 17/1659* (2013.01); *A61B 17/32* (2013.01); *A61B 17/3421* (2013.01); *A61L 31/005* (2013.01); *A61L 31/022* (2013.01); *A61L 31/16* (2013.01); *A61B 17/3201* (2013.01); *A61B 17/3211* (2013.01); *A61B 17/320016* (2013.01); *A61B 17/320708* (2013.01); *A61B 2217/005* (2013.01)

(58) Field of Classification Search
CPC ............ A61B 17/1615; A61B 17/1613; A61B 17/1633; A61B 17/1655
See application file for complete search history.

(56) References Cited

U.S. PATENT DOCUMENTS

| | | | | |
|---|---|---|---|---|
| 5,522,817 A | * | 6/1996 | Sander | A61B 17/0642 606/77 |
| 5,755,718 A | * | 5/1998 | Sklar | A61B 17/1764 606/88 |

(Continued)

FOREIGN PATENT DOCUMENTS

| | | |
|---|---|---|
| WO | 2016142749 A1 | 9/2016 |
| WO | 2019145532 A1 | 8/2019 |

*Primary Examiner* — Matthew J Lawson
(74) *Attorney, Agent, or Firm* — Total Awareness Consulting Services; Robert Winslow

(57) ABSTRACT

Medical devices are disclosed. For example, a medical device includes an elongated member. The medical device includes a hole forming surface along a portion of the elongated member. The medical device includes an open cell element in physical communication with the elongated member. The open cell element is configured to house at least a first portion of a biocompatible substance.

19 Claims, 23 Drawing Sheets

(56) References Cited

U.S. PATENT DOCUMENTS

| | | | |
|---|---|---|---|
| 6,547,792 B1* | 4/2003 | Tsuji | A61B 17/68 606/77 |
| 7,029,479 B2 | 4/2006 | Fallarida et al. | |
| 7,604,617 B2* | 10/2009 | Porter | H04R 25/65 623/10 |
| 8,303,598 B2 | 11/2012 | Frankel et al. | |
| 9,622,760 B2* | 4/2017 | Brandt | A61B 17/1717 |
| 2001/0023349 A1* | 9/2001 | VanTassel | A61M 5/3286 606/53 |
| 2004/0064058 A1* | 4/2004 | McKay | A61F 2/4601 600/506 |
| 2004/0220576 A1 | 11/2004 | Sklar et al. | |
| 2006/0149268 A1* | 7/2006 | Truckai | A61B 17/1617 606/79 |
| 2006/0195094 A1* | 8/2006 | McGraw | A61B 17/7098 606/279 |
| 2007/0167681 A1 | 7/2007 | Gill et al. | |
| 2008/0033463 A1 | 2/2008 | Stoken | |
| 2008/0058816 A1* | 3/2008 | Philippon | A61B 17/8888 606/326 |
| 2010/0286616 A1* | 11/2010 | Baroud | A61B 17/3472 604/164.11 |
| 2012/0238906 A1 | 9/2012 | Gilchrest et al. | |
| 2013/0267999 A1* | 10/2013 | Ng | A61B 17/1615 606/232 |
| 2015/0157370 A1* | 6/2015 | Gross | A61B 17/7241 606/62 |
| 2021/0290218 A1* | 9/2021 | Housman | A61B 17/8645 |

\* cited by examiner

DEVICE WITH AN OPEN CELL ELEMENT

CROSS-REFERENCE TO RELATED APPLICATIONS

This application claims the benefit of U.S. Provisional Application No. 62/769,662, filed Nov. 20, 2018, which is hereby incorporated by reference in its entirety.

BACKGROUND

During many orthopedic surgeries, holes need to be created in bone or cartilage prior to fastener installation. Examples of fasteners installed during orthopedic surgeries include but are not limited to: bone screws and anchors. Creating a hole and securing a fastener are often two distinct tasks. During these surgeries, especially those that include arthroscopy, orthopedic surgeons often lose time trying to locate a hole that was drilled prior to the fastener installation. This may be due to, for example, fluid and surrounding tissue obscuring the hole after the device used to create the hole is removed. Many orthopedic surgeons use biocompatible ink from a pen to color a cutting surface of a cutting tool (for example, a drill bit or a punch) just prior to use. There are many shortcomings with this technique which may include, but are not limited to: additional time required to load the ink onto the cutting surface, the cutting surface may hold a limited amount of ink that is insufficient, the ink may be quickly removed once the cutting surface is engaged in the bone or cartilage, most if not all of the ink may be applied to material that is removed, and the mark, if any, left by the ink on the surrounding tissue may not be sufficient to see with a naked eye during surgery. In many cases, a hole may be filled or covered with fluid or surrounding tissue after the hole is created and before a fastener can be located in the hole.

Many existing hole forming medical devices may not be configured to house biocompatible substances for eventual delivery during their use in the target physiological environment. Many existing hole forming medical devices may comprise closed cells such as, for example, a syringe. Many existing hole forming medical devices may not be configured to deliver biocompatible substances to a surgical site simultaneously or near simultaneously with the primary hole forming function.

Many existing biopsy tools configured to employ dye to mark a biopsy site may not be configured to successfully mark surrounding bone, cartilage, and/or soft tissue. Many existing tools configured to inject dye into a tumor may not be configured to successfully mark surrounding bone, cartilage, and/or soft tissue. Many existing surgical marking methods require multiple steps to form a hole or trim a portion of bone, cartilage, and/or soft tissue, and mark the hole or tissue surrounding the trimmed portion. Additional steps may be required to treat an affected area. For example, a plunger of a syringe may need to be drawn back and/or advanced. Many existing devices configured to deliver biocompatible substances may require physical containment of the biocompatible substance during introduction to a physiological environment. Many existing devices configured to deliver biocompatible substances may require a physical action by the user to load the biocompatible substance into the device prior to use.

What is needed are improved devices and methods configured to deliver a substance.

DETAILED DESCRIPTION OF EMBODIMENTS

Figure 1:
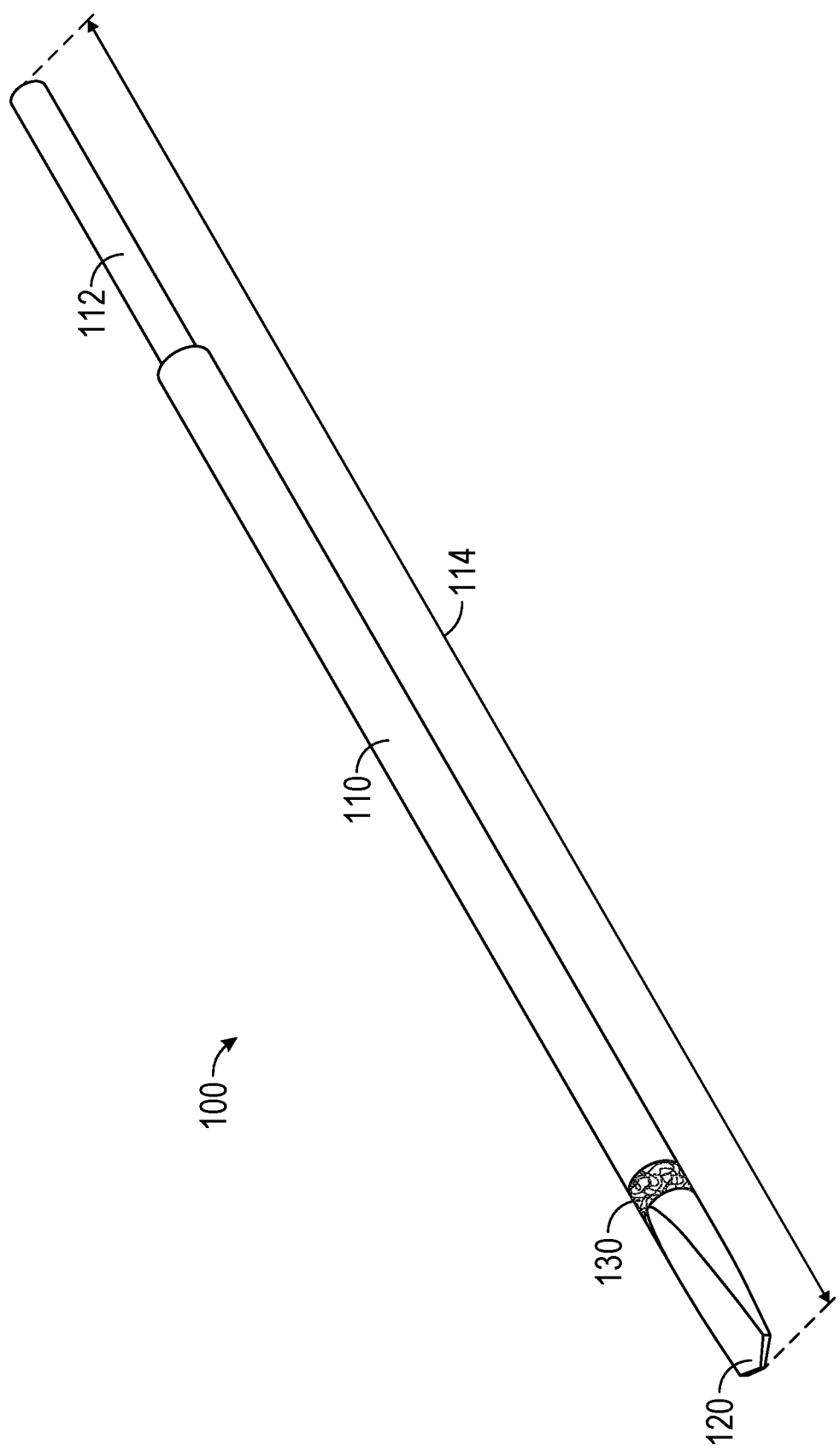
FIG. 1 illustrates an isometric view of an example device as per an aspect of an embodiment.

Embodiments of the present disclosure include a medical device. More specifically, embodiments of the present disclosure include a medical device comprising at least one open cell element. For the purpose of the present disclose, an open cell element comprises a plurality of cells, holes, or cavities, that are at least partially open to the surrounding environment.

Various embodiments may be employed to reduce a duration of an orthopedic or arthroscopic surgery.

Various embodiments may be employed to provide more effective delivery of biocompatible substances to target tissue and/or physiological environments.

According to an embodiment, a medical device may comprise an elongated member. The elongated member may comprise a solid material. The elongated member may be non-cannulated. The medical device may comprise a hole forming surface. The hole forming surface may be configured to form a hole in a physiological environment. The physiological environment may be at least part of a human being, mammal, and/or animal. The hole forming surface may be along a portion of the elongated member. The hole forming surface may be part of an element attached to the elongated member. The hole forming surface may comprise a cutting surface. A hole may be formed in a physiological environment without cutting. For example, two or more tendons and/or ligaments could be separated from each other. For example, fascia could be separated from other tissue. The medical device may comprise an open cell element. The open cell element may be in physical communication with the elongated member. The open cell element may be configured to house at least a portion of a biocompatible substance. The at least a portion of the biocompatible substance may be applied and at least partially dried, set, infused, combinations thereof, and/or the like by a manufacturer. The at least a portion of the biocompatible substance may be applied and at least partially dried, set, infused, combinations thereof, and/or the like by a user prior to use. Dried portions of the biocompatible substance may rehydrate when inserted into a physiological environment.

According to an embodiment, a medical device may be configured to be employed as a drill bit, a tap, a punch, a burr, a file, a cutter, a shaver, a cannula, a probe, a retractor, a stitching needle, combinations thereof, and/or the like. Examples of the cutter include but are not limited to a curette, a knife, a pair of scissors, combinations thereof, and/or the like. The stitching needle may also be referred to as a closure device, or a suture needle. The medical device may be configured to form a hole in bone, cartilage, skin, muscle, fascia, a tendon, a ligament, adipose tissue, scar tissue, combinations thereof, and/or the like. The hole may be formed within one tissue structure. The hole may be formed in between two or more tissue structures. The medical device may be configured to enlarge a hole in bone, cartilage, skin, muscle, fascia, a tendon, a ligament, adipose tissue, scar tissue, combinations thereof, and/or the like. The medical device may be configured to deliver a biocompatible substance to the hole. The medical device may be configured to cut a section of bone, cartilage, skin, muscle, fascia, a tendon, a ligament, adipose tissue, scar tissue, combinations thereof, and/or the like. The medical device may be configured to shave a section of bone, cartilage, skin, muscle, fascia, a tendon, a ligament, adipose tissue, scar tissue, combinations thereof, and/or the like. The medical device may be configured to deliver a biocompatible substance to the section. The section may comprise a section area at least partially surrounding the piece or pieces that have been cut away and/or removed.

According to an embodiment, a hole forming surface may comprise a first material. The first material may comprise tungsten carbide and/or titanium carbide. An open cell element may comprise a second material. At least one of the first material and the second material may comprise surgical stainless steel. At least one of the first material and the second material may comprise a titanium alloy, a stainless steel alloy, a cobalt-chromium alloy, carbon fiber, a polymer, a ceramic, combinations thereof, and/or the like. The surgical stainless steel may be implant grade and/or biocompatible. At least one of the first material and the second material may comprise porous stainless steel. A porosity may be inherent to the first material and/or the second material. The porosity may be created using a secondary process (e.g. sintering). The hole forming surface may comprise a first porosity. The first porosity may be infinitesimally small. For example, the first porosity may be less than 1 percent by volume. The first porosity may be zero. The open cell element may comprise a second porosity. The second porosity may be based on a specific biocompatible substance.

According to an embodiment, a biocompatible substance may comprise an ink, a dye, a stain, an analgesic agent, a medication, a coagulant, patient blood, stem cells, an anti-inflammatory agent, a hemostatic agent, an antibacterial agent, a bio-stimulatory agent, combinations thereof, and/or the like. Examples of the bio-stimulatory agent include but are not limited to hyaluronic acid and chondroitin. At least some of the biocompatible substance may comprise liquid. At least some of the biocompatible substance may be dry.

FIG. 1 illustrates an isometric view of an example medical device 100 as per an aspect of an embodiment. The medical device 100 may comprise an elongated member 110. The medical device 100 may comprise a hole forming surface 120. The hole forming surface 120 may comprise a first material. The medical device 100 may comprise an open cell element 130. The open cell element 130 may comprise a second material. The medical device 100 may comprise a shank 112. The medical device 100 may comprise an overall length 114. The overall length 114 may be based on the size of a target body part (for example, the size of a bone). The overall length 114 may be based on a distance to reach a target body part inside a body.

Figure 2:
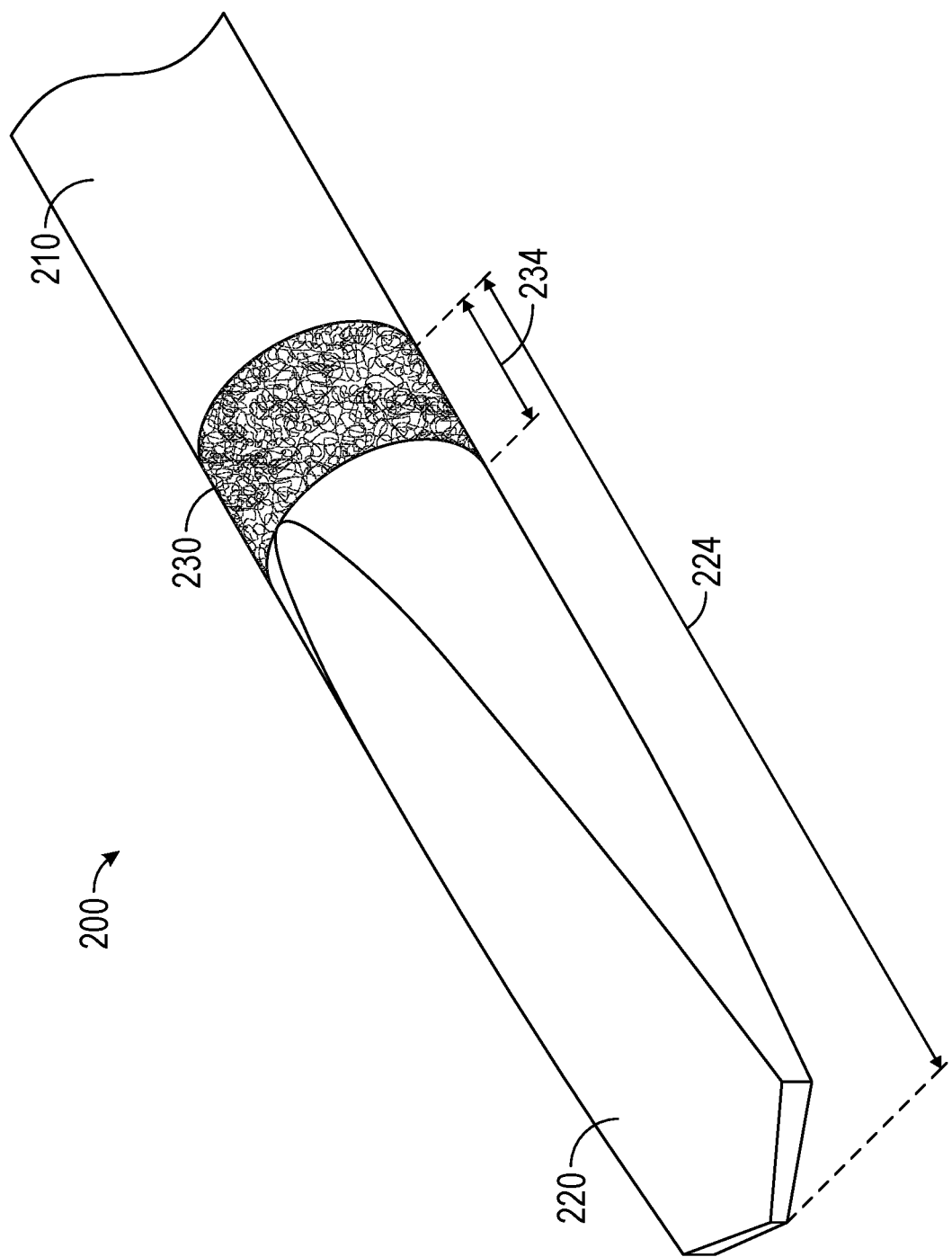
FIG. 2 illustrates an isometric view of a portion of an example device as per an aspect of an embodiment.

FIG. 2 illustrates an isometric view of a portion of an example medical device 200 as per an aspect of an embodiment. The medical device 200 may comprise an elongated member 210. The medical device 200 may comprise a hole forming surface 220. The hole forming surface 220 may comprise a first material. The medical device 200 may comprise an open cell element 230. The open cell element 230 may comprise a marking depth 234. The open cell element 230 may comprise a second material. A distance from the tip of the hole forming surface 220 to the end of the open cell element 230 may comprise a target hole forming depth 224. Once the elongated member 210 is employed to form a hole that reaches the target hole forming depth 224, the marking depth 234 of the open cell element 230 may be employed to mark the opening of the hole.

Figure 3:
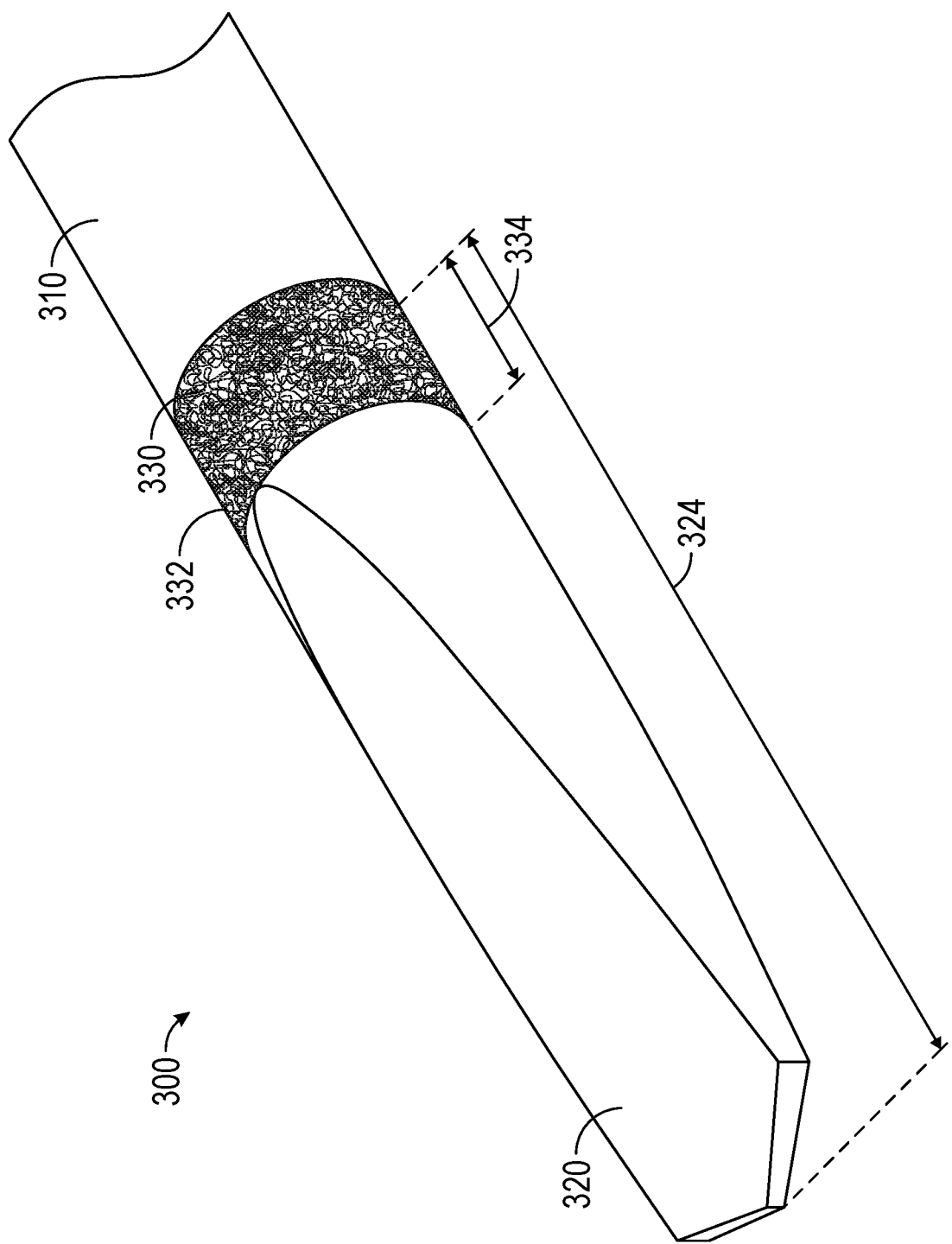
FIG. 3 illustrates an isometric view of a portion of an example device with a substance as per an aspect of an embodiment.

FIG. 3 illustrates an isometric view of a portion of an example medical device 300 with a biocompatible substance as per an aspect of an embodiment. The medical device 300 may comprise an elongated member 310. The medical device 300 may comprise a hole forming surface 320. The hole forming surface 320 may comprise a first material. The medical device 300 may comprise an open cell element 330. The open cell element 330 may comprise a marking depth 334. The open cell element 330 may comprise a second material. The open cell element 330 may comprise a plurality of open cells 332. The plurality of open cells 332 may be created by removing material from the second material. For example, material may be etched from the second material to create the plurality of open cells 332. The plurality of open cells 332 may be created by removing material from the elongated member 310. For example, material may be etched from the elongated member 310 to create the plurality of open cells 332. The open cell element 330 may be configured to house at least a portion of the biocompatible substance through employment of the plurality of open cells 332. At least some of the biocompatible substance may be dry. A distance from the tip of the hole forming surface 320 to the end of the open cell element 330 may comprise a target hole forming depth 324.

According to an embodiment, an open cell element may be configured to release at least some of a biocompatible substance upon entrance of the open cell element into a physiological environment. The open cell element may be configured to accelerate the release of the biocompatible substance with rotation of an elongated member. A rate of acceleration may be based on a rotational acceleration of the elongated member. The open cell element may be configured to directionalize the release of the biocompatible substance with rotation of the elongated member. Directionalization may be based on the structure of open cells in the open cell element and/or the orientation of the open cells in the open cell element.

According to an embodiment, an open cell element may be incorporated with an elongated member. For the purpose of the present disclose, incorporated may be interpreted as in physical communication with. For example, a first component incorporated with a second component may include two distinct components. For example, a first component incorporated with a second component may include a portion of a second component that has been modified to create the first component. The open cell element may comprise a ring, a sleeve, a collar, a segment of the elongated member, an additional segment, combinations thereof, and/or the like. The ring may comprise an outer diameter equal to or nearly equal to the outer diameter of a hole forming surface. The ring may comprise a tapered outer profile. The tapered outer profile may be employed, for example, to countersink fasteners. The tapered outer profile may be employed to create a rounded edge on holes formed. Rounded edges may be employed to reduce the incidence of frayed sutures. The sleeve may be configured to slide over and/or slide along at least a portion of the elongated member. The collar may comprise an outer diameter larger than the outer diameter of a hole forming surface. The collar may be employed, for example, to mark a top surface surrounding a formed hole. The open cell element may be fastened to the elongated member.

Figure 4:
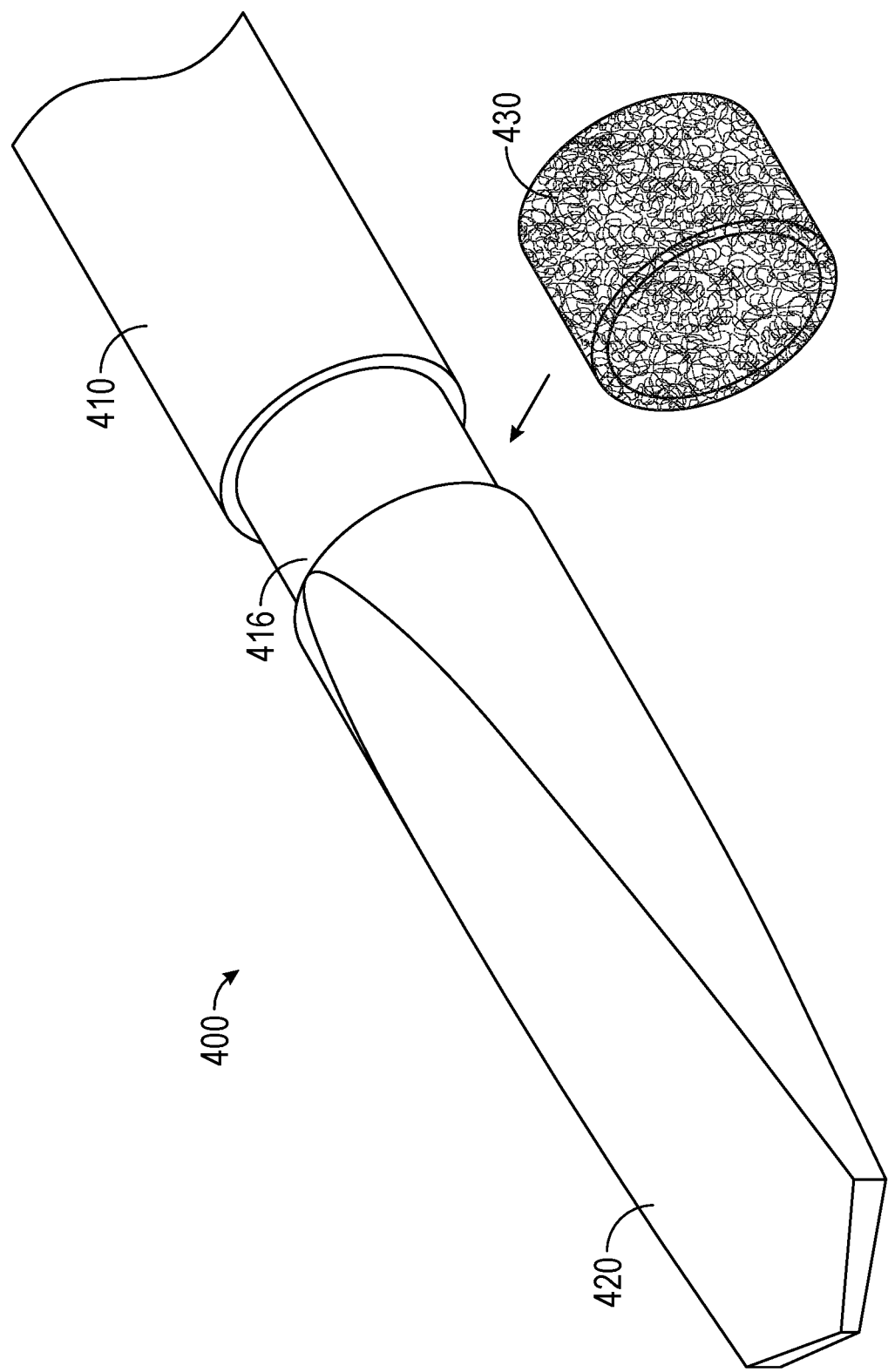
FIG. 4 illustrates an isometric view of a portion of an example device and an example open cell element as per an aspect of an embodiment.

FIG. 4 illustrates an isometric view of a portion of an example medical device 400 and an example open cell element 430 as per an aspect of an embodiment. The medical device 400 may comprise an elongated member 410. The medical device 400 may comprise a hole forming surface 420. The hole forming surface 420 may comprise a first material. The medical device 400 may comprise the open cell element 430. The open cell element 430 may comprise a second material. The open cell element 430 may be configured to house at least a portion of a biocompatible substance. At least some of the biocompatible substance may be dry. The open cell element 430 may comprise a ring. The open cell element 430 may be configured for connection to the relief 416 in the elongated member 410. The open cell element 430 may be disposed to the relief 416 in the elongated member 410.

Figure 5B:
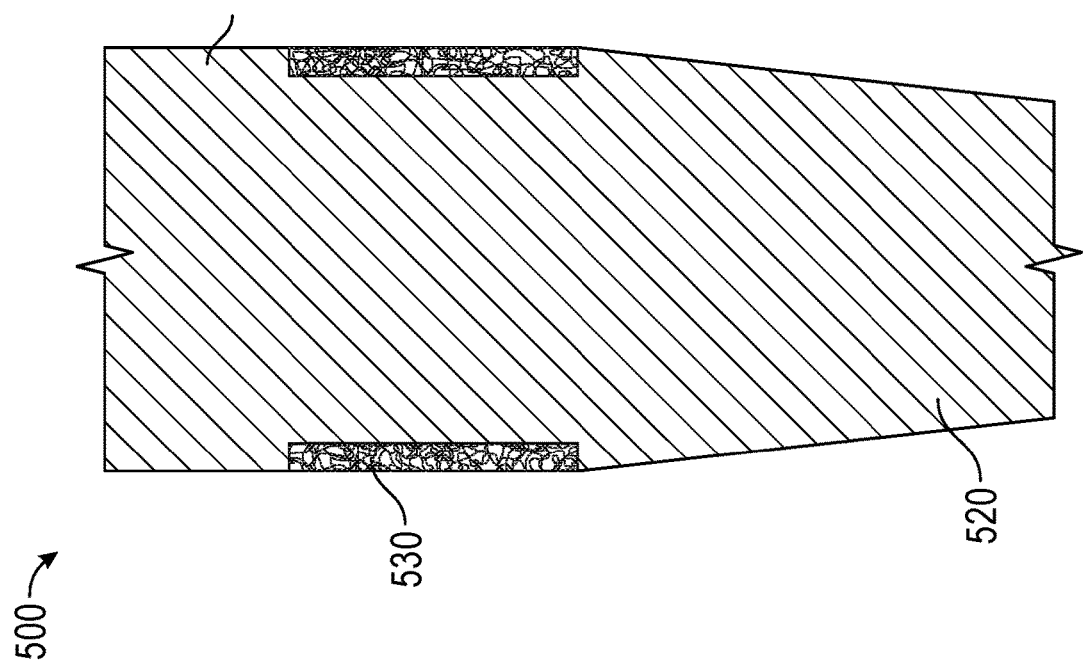
FIGS. 5A and 5B illustrate cross-sectional views of an example device as per various aspects of an embodiment.
Figure 5A:
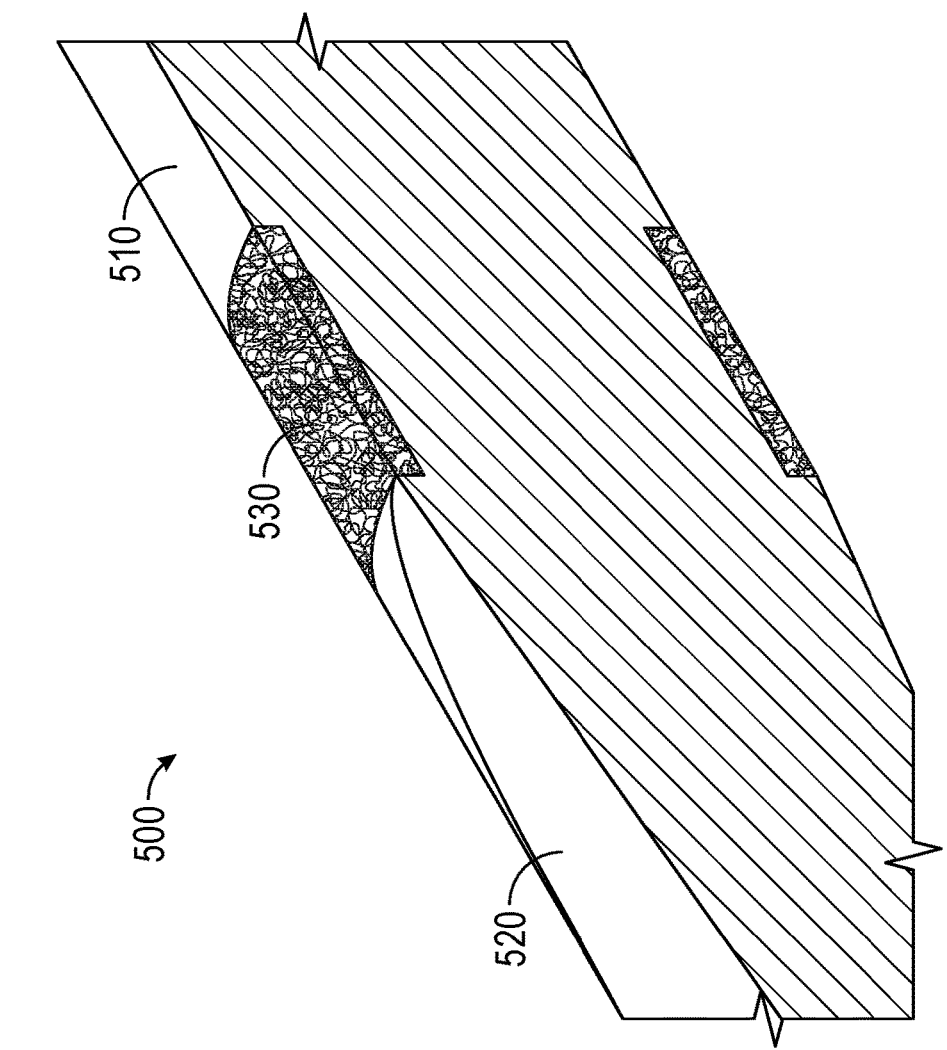

FIGS. 5A and 5B illustrate cross-sectional views of an example medical device 500 as per various aspects of an embodiment. The medical device 500 may comprise an elongated member 510. The medical device 500 may comprise a hole forming surface 520. The hole forming surface 520 may comprise a first material. The medical device 500 may comprise an open cell element 530. The open cell element 530 may comprise a second material.

According to an embodiment, an elongated member may comprise a well. The well may comprise a hollow compartment, a recessed area, a depression, combinations thereof, and/or the like. The well may be structured to hold a substance. The well may be surrounded by an open cell element. The well may be configured to house at least a portion of a biocompatible substance. At least some of the biocompatible substance may be dry. The well may comprise a cross-sectional relief, a vertical relief, a plurality of micro-holes, a plurality of dimples, combinations thereof, and/or the like.

Figure 6:
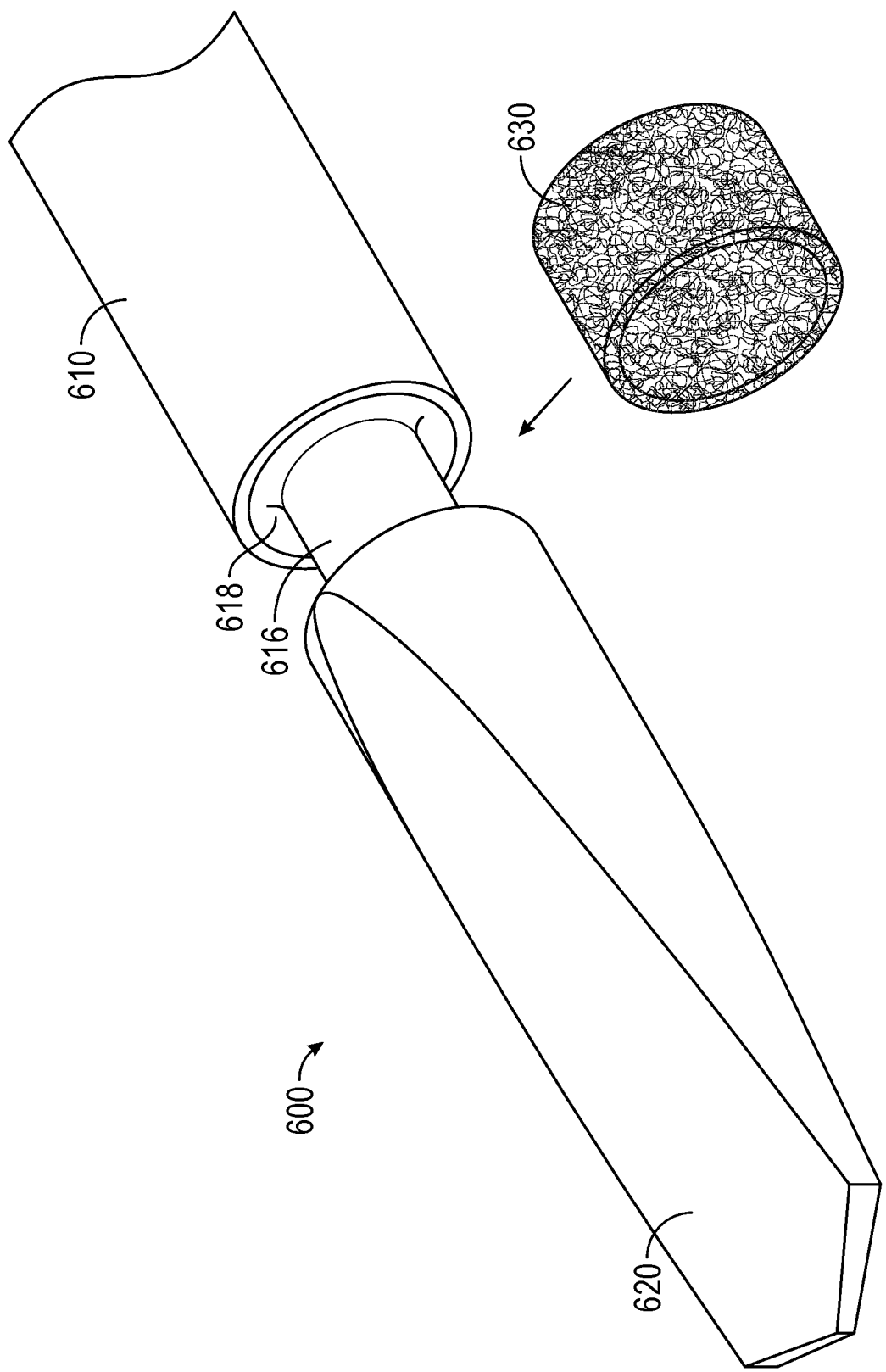
FIG. 6 illustrates an isometric view of an example device and an example open cell element as per an aspect of an embodiment.

FIG. 6 illustrates an isometric view of an example medical device 600 and an example open cell element as per an aspect of an embodiment. The medical device 600 may comprise an elongated member 610. The medical device 600 may comprise a hole forming surface 620. The hole forming surface 620 may comprise a first material. The medical device 600 may comprise the open cell element 630. The open cell element 630 may comprise a second material. The open cell element 630 may be configured to house at least a first portion of a biocompatible substance. At least some of the biocompatible substance may be dry. The open cell element 630 may comprise a ring. The open cell element 630 may be configured for installation over a relief 616 in the elongated member 610. The open cell element may be disposed to the relief 616 in the elongated member 610. The elongated member 610 may comprise a well shoulder 618. The well shoulder 618 may be configured to create a well under the open cell element 630 once the open cell element 630 is disposed to the elongated member 610. The well may be configured to house at least a second portion of the biocompatible substance. The open cell element 630 may be configured for connection to the well shoulder 618 of the elongated member 610.

Figure 7B:
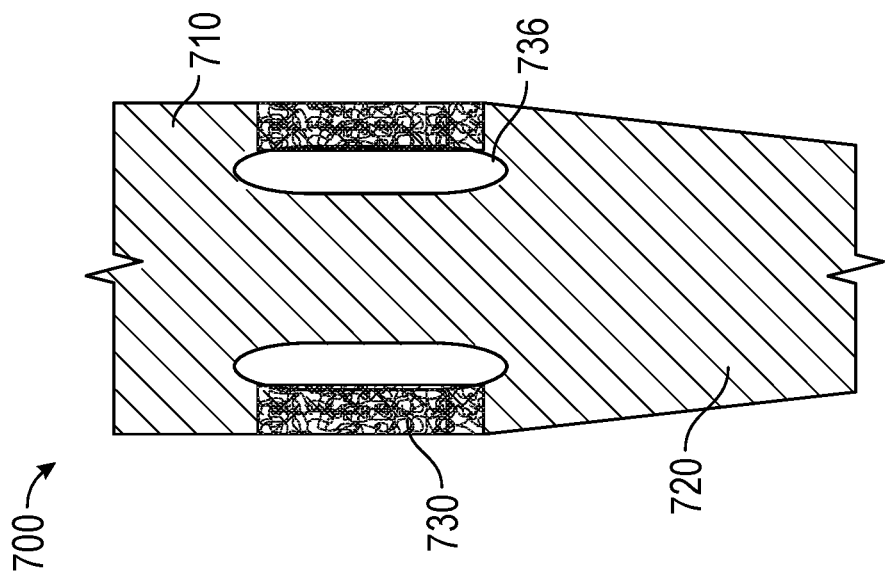
FIGS. 7A and 7B illustrate cross-sectional views of an example device as per various aspects of an embodiment.
Figure 7A:
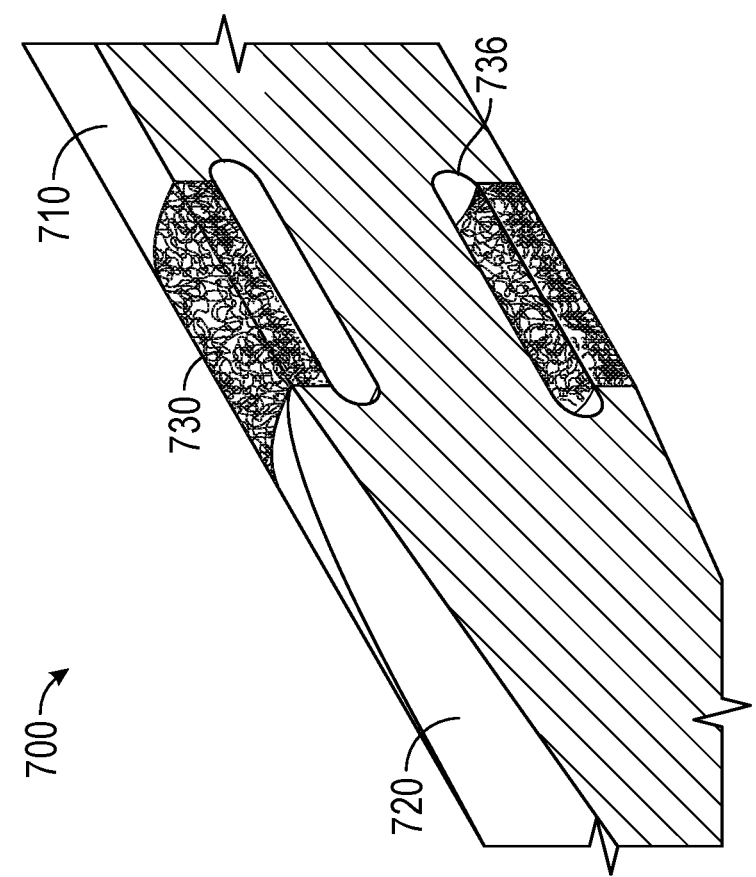

FIGS. 7A and 7B illustrate cross-sectional views of an example medical device 700 as per various aspects of an embodiment. The medical device 700 may comprise an elongated member 710. The medical device 700 may comprise a hole forming surface 720. The hole forming surface 720 may comprise a first material. The medical device 700 may comprise an open cell element 730. The open cell element 730 may comprise a second material. The open cell element 730 may be configured to house at least a first portion of a biocompatible substance. At least some of the biocompatible substance may be dry. The open cell element 730 may comprise a ring. The open cell element 730 may be disposed to a well 736. The well 736 may be configured to house at least a second portion of the biocompatible substance.

Figure 8:
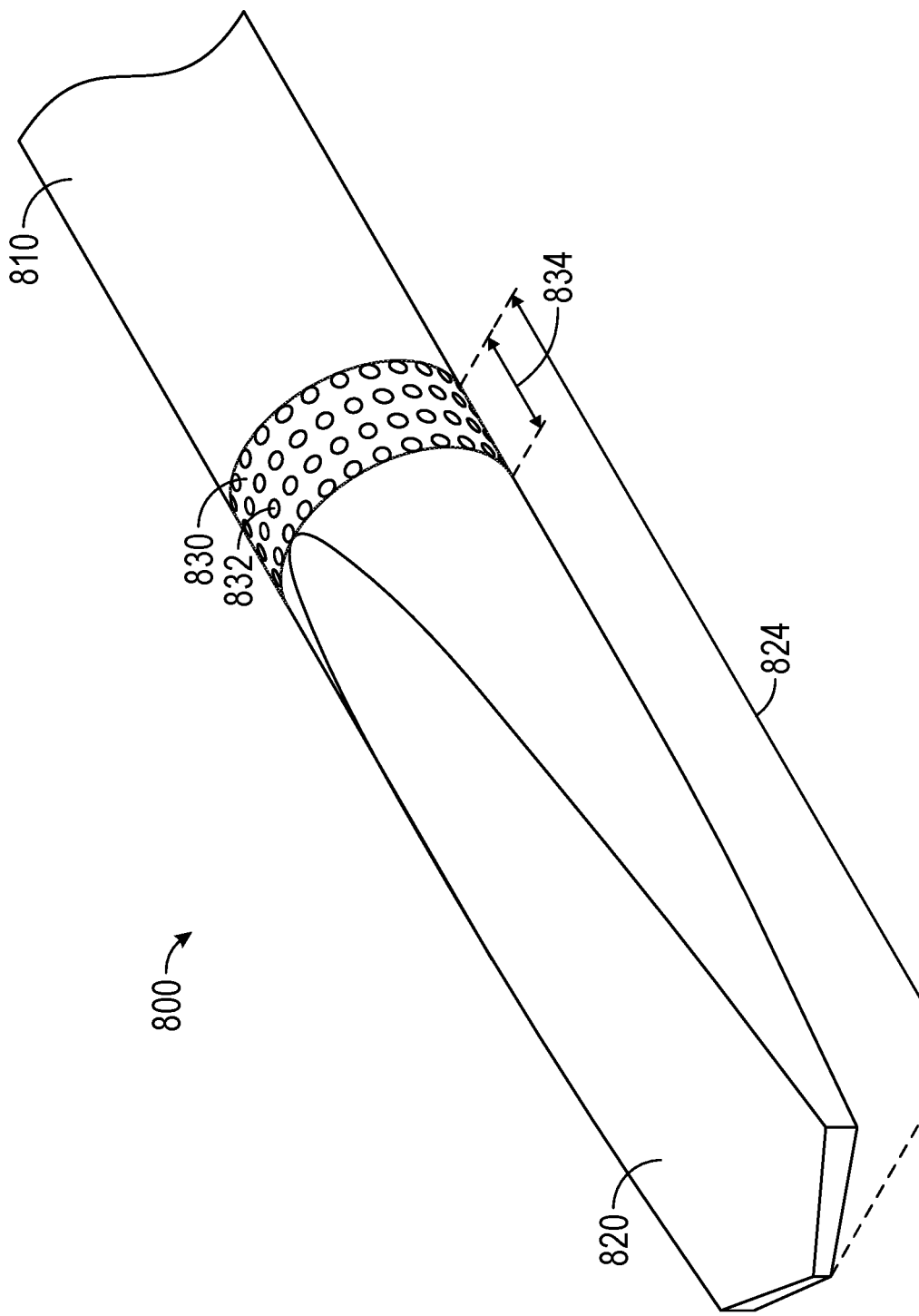
FIG. 8 illustrates an isometric view of a portion of an example device as per an aspect of an embodiment.

FIG. 8 illustrates an isometric view of a portion of an example medical device 800 as per an aspect of an embodiment. The medical device 800 may comprise an elongated member 810. The medical device 800 may comprise a hole forming surface 820. The hole forming surface 820 may comprise a first material. The medical device 800 may comprise an open cell element 830. The open cell element 830 may comprise a marking depth 834. The open cell element 830 may comprise a second material. The open cell element 830 may comprise a plurality of open cells 832. The plurality of open cells 832 may be created by removing material from the second material. For example, the second material may be drilled to create the plurality of open cells 832. The plurality of open cells 832 may be created by removing material from the elongated member 810. For example, the elongated member 810 may be drilled to create the plurality of open cells 832. A distance from the tip of the hole forming surface 820 to the end of the open cell element 830 may comprise a target hole forming depth 824.

Figure 9:
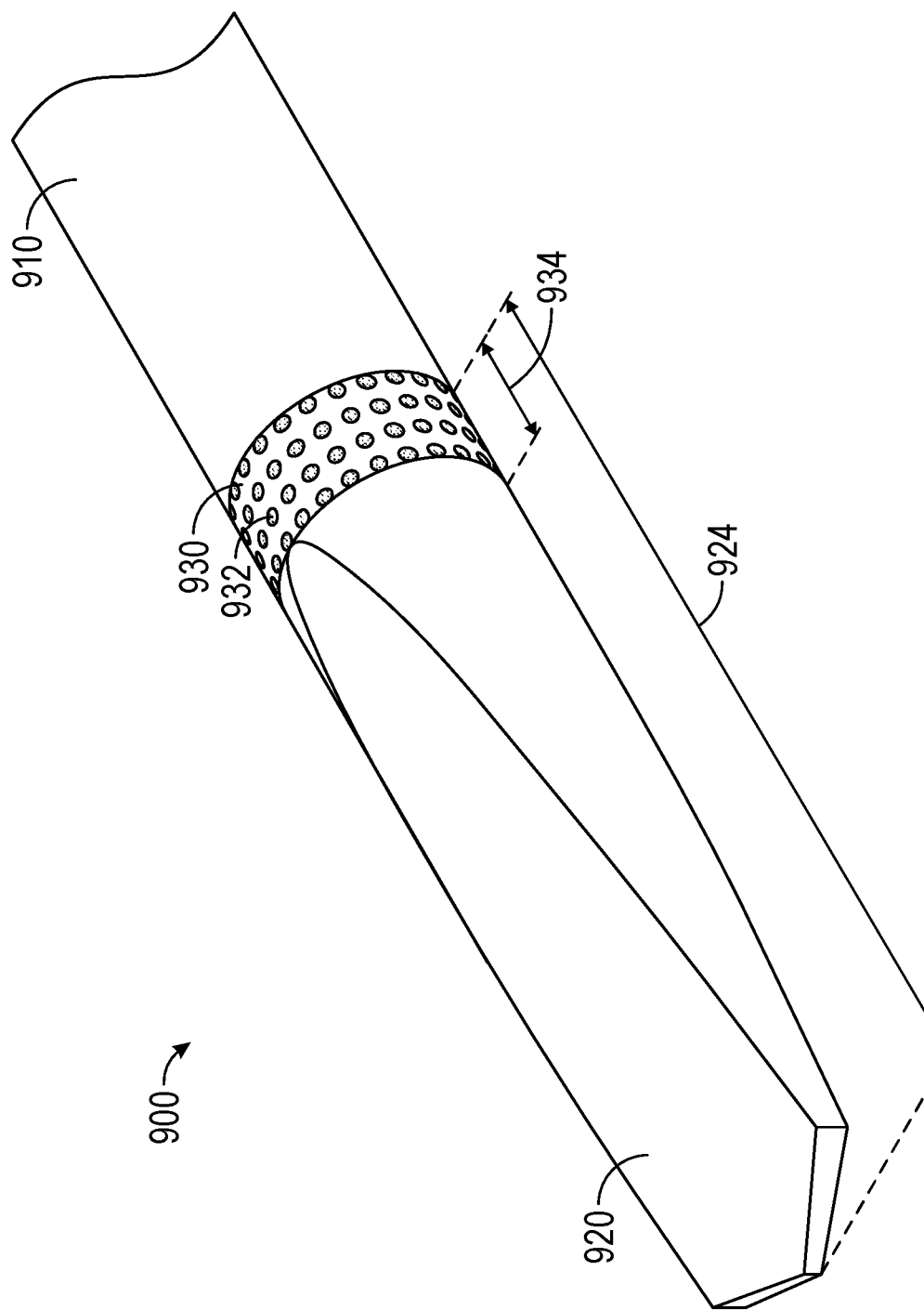
FIG. 9 illustrates an isometric view of a portion of an example device with a substance as per an aspect of an embodiment.

FIG. 9 illustrates an isometric view of a portion of an example medical device 900 with a biocompatible substance as per an aspect of an embodiment. The medical device 900 may comprise an elongated member 910. The medical device 900 may comprise a hole forming surface 920. The hole forming surface 920 may comprise a first material. The medical device 900 may comprise an open cell element 930. The open cell element 930 may comprise a marking depth 934. The open cell element 930 may comprise a second material. The open cell element 930 may comprise a plurality of open cells 932. The plurality of open cells 932 may be created by removing material from the second material. For example, the second material may be drilled to create the plurality of open cells 932. The plurality of open cells 932 may be created by removing material from the elongated member 910. For example, the elongated member 910 may be drilled to create the plurality of open cells 932. The open cell element 930 may be configured to house at least a portion of the biocompatible substance through employment of the plurality of open cells 932. At least some of the biocompatible substance may be dry. A distance from the tip of the hole forming surface 920 to the end of the open cell element 930 may comprise a target hole forming depth 924.

Figure 10:
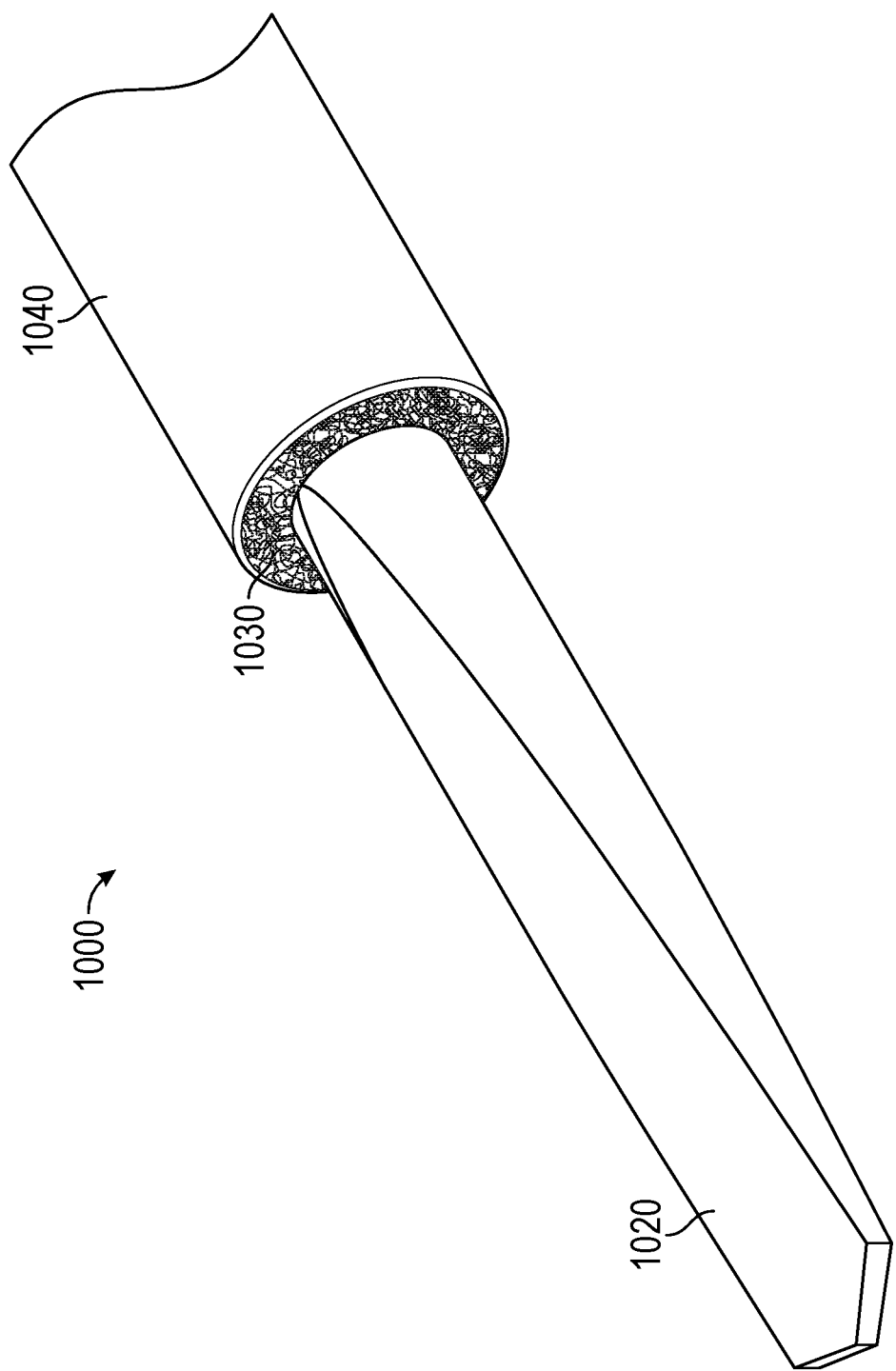
FIG. 10 illustrates an isometric view of a portion of an example device as per an aspect of an embodiment.

FIG. 10 illustrates an isometric view of a portion of an example medical device 1000 as per an aspect of an embodiment. The medical device 1000 may comprise an elongated member. The medical device 1000 may comprise a hole forming surface 1020. The hole forming surface 1020 may comprise a first material. The medical device 1000 may comprise an open cell element 1030. The open cell element 1030 may comprise at least one second material. The open cell element 1030 may comprise a collar 1040. The collar 1040 may be employed, for example, to mark a top surface surrounding a formed hole. The top surface surrounding the formed hole may be marked through employment of a biocompatible substance at least partially housed in the open cell element 1030.

Figure 11:
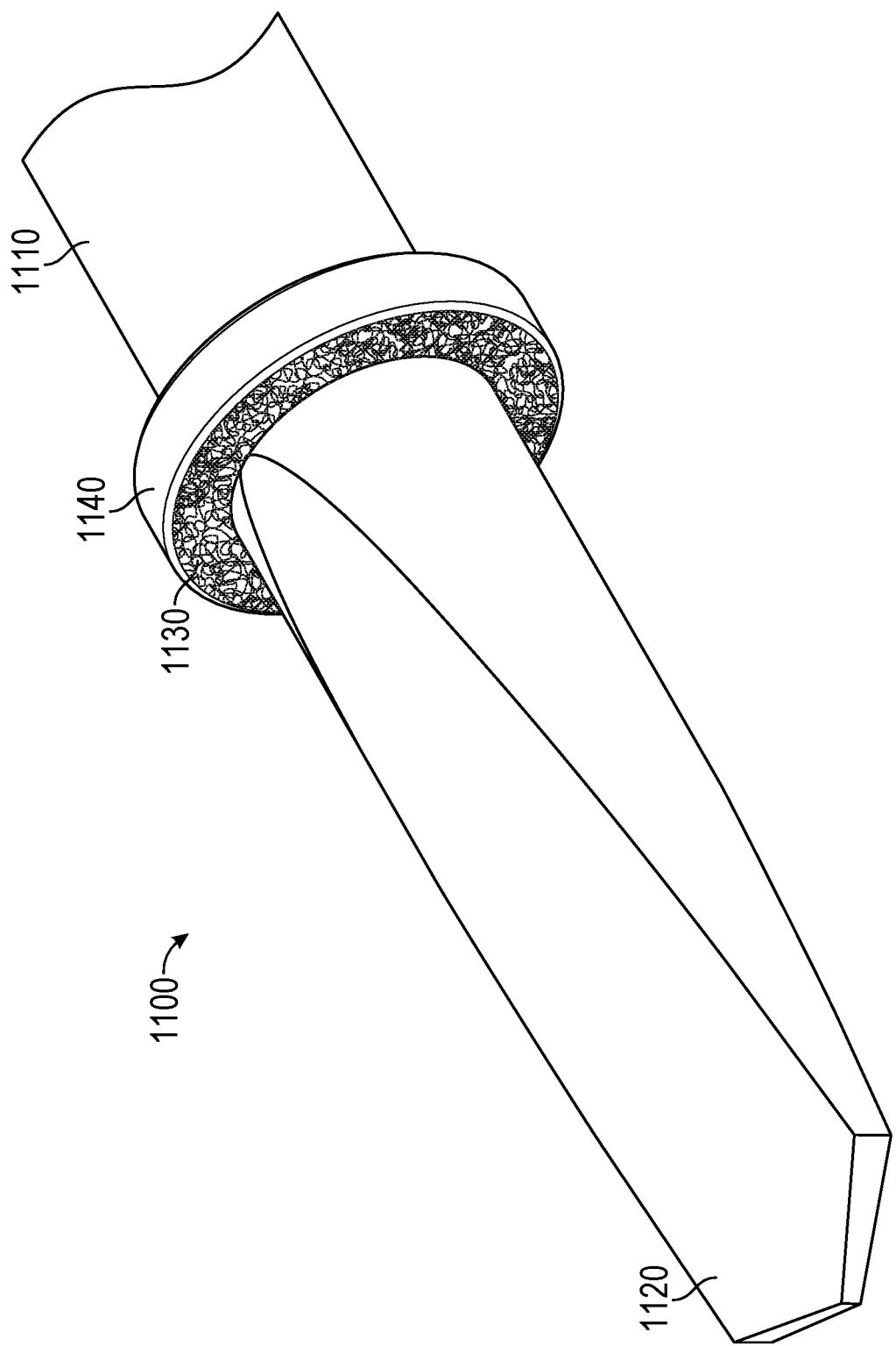
FIG. 11 illustrates an isometric view of a portion of an example device as per an aspect of an embodiment.

FIG. 11 illustrates an isometric view of a portion of an example medical device 1100 as per an aspect of an embodiment. The medical device 1100 may comprise an elongated member 1110. The medical device 1100 may comprise a hole forming surface 1120. The hole forming surface 1120 may comprise a first material. The medical device 1100 may comprise an open cell element 1130. The open cell element 1130 may comprise at least one second material. The open cell element 1130 may comprise a collar 1140. The collar 1140 may be employed to mark a top surface surrounding a formed hole. The top surface surrounding the formed hole may be marked through employment of a biocompatible substance at least partially housed in the open cell element 1130.

Figure 12:
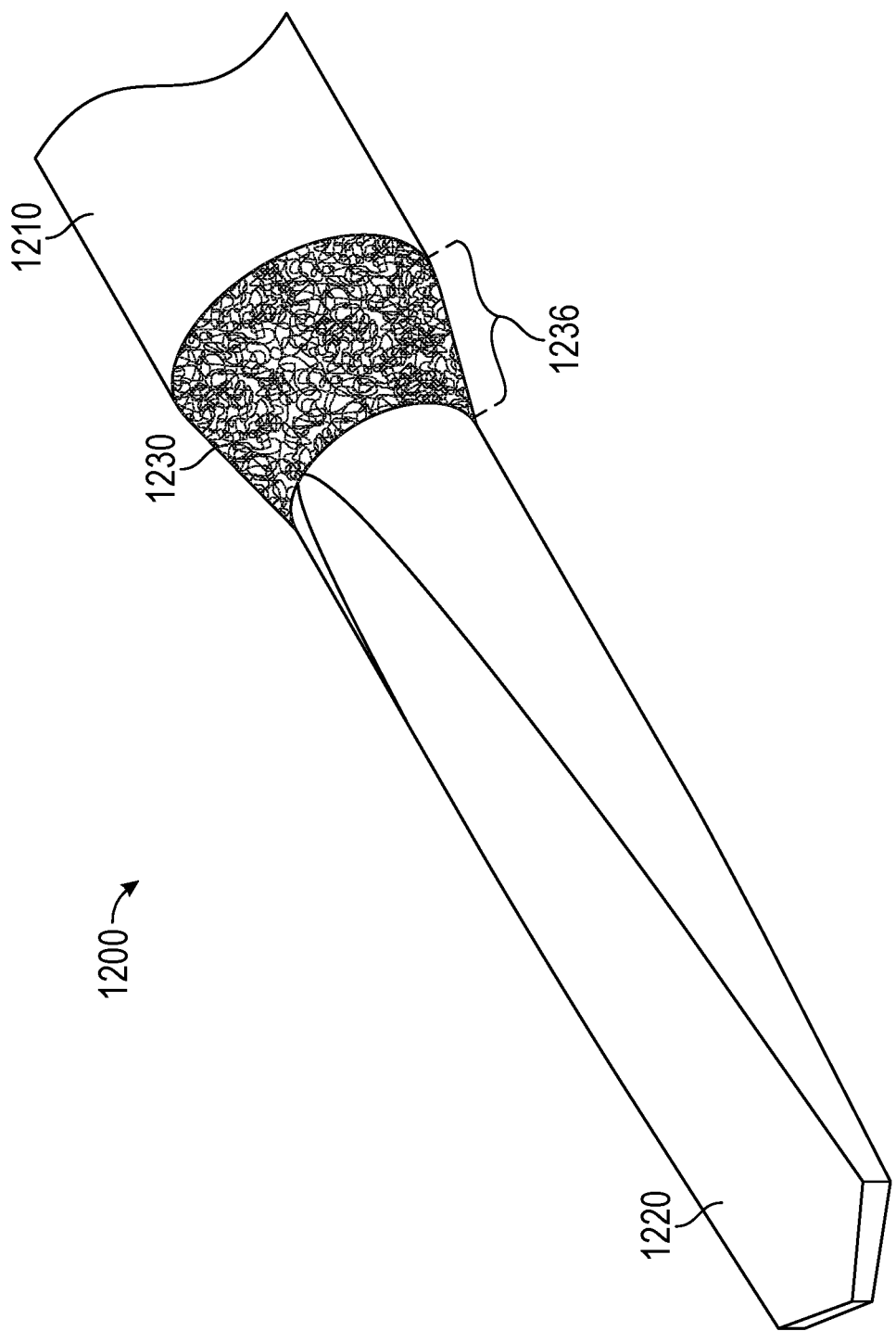
FIG. 12 illustrates an isometric view of a portion of an example device as per an aspect of an embodiment.

FIG. 12 illustrates an isometric view of a portion of an example medical device 1200 as per an aspect of an embodiment. The medical device 1200 may comprise an elongated member 1210. The medical device 1200 may comprise a hole forming surface 1220. The hole forming surface 1220 may comprise a first material. The medical device 1200 may comprise an open cell element 1230. The open cell element 1230 may comprise a tapered outer profile. The open cell element 1230 may comprise a marking range 1236. The open cell element 1230 may comprise a second material.

Figure 13:
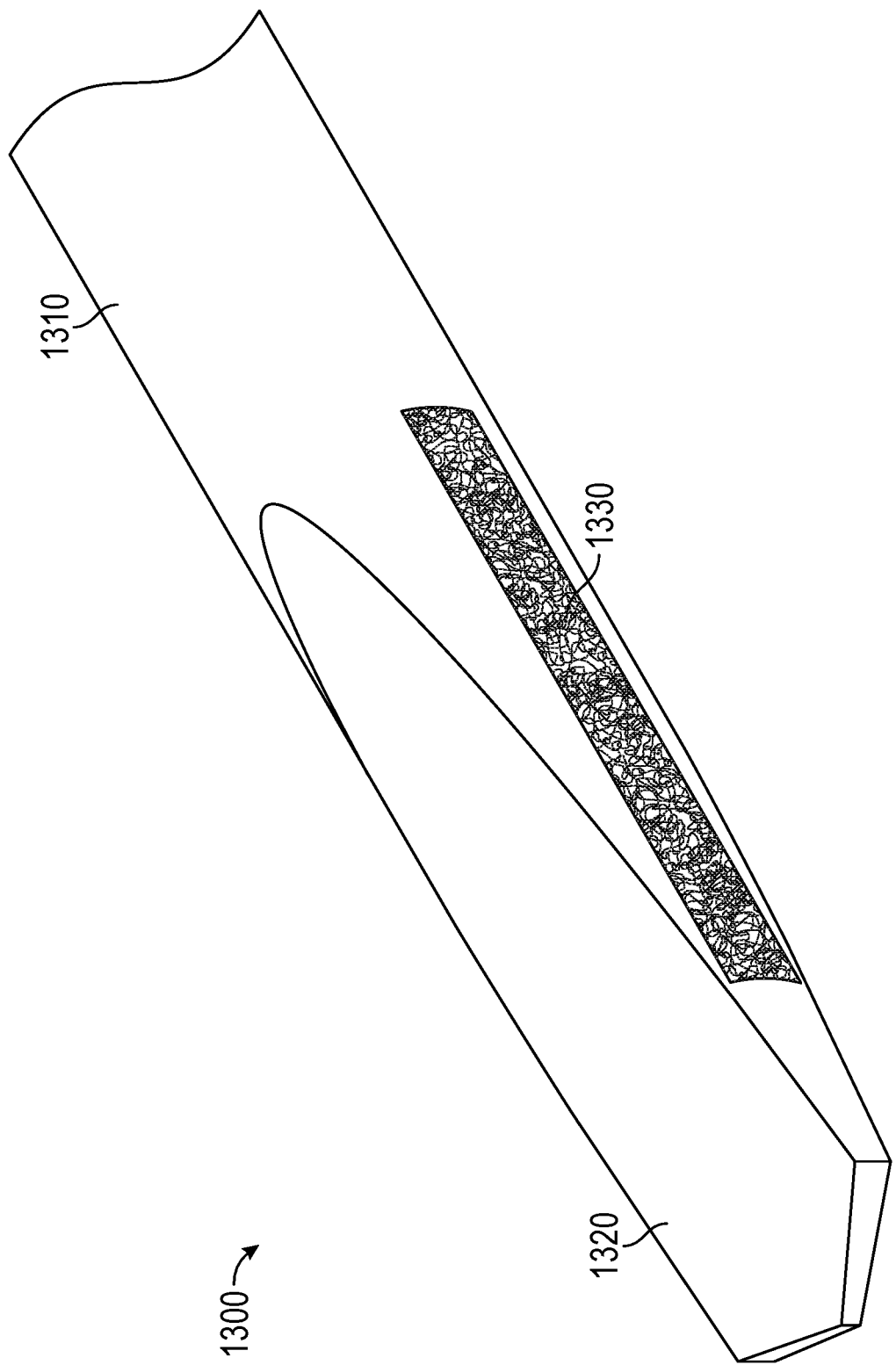
FIG. 13 illustrates an isometric view of a portion of an example device as per an aspect of an embodiment.

FIG. 13 illustrates an isometric view of a portion of an example medical device 1300 as per an aspect of an embodiment. The medical device 1300 may comprise an elongated member 1310. The medical device 1300 may comprise a hole forming surface 1320. The hole forming surface 1320 may comprise a first material. The medical device 1300 may comprise an open cell element 1330. The open cell element 1330 may comprise an additional segment. The open cell element 1330 may comprise a second material.

Figure 14:
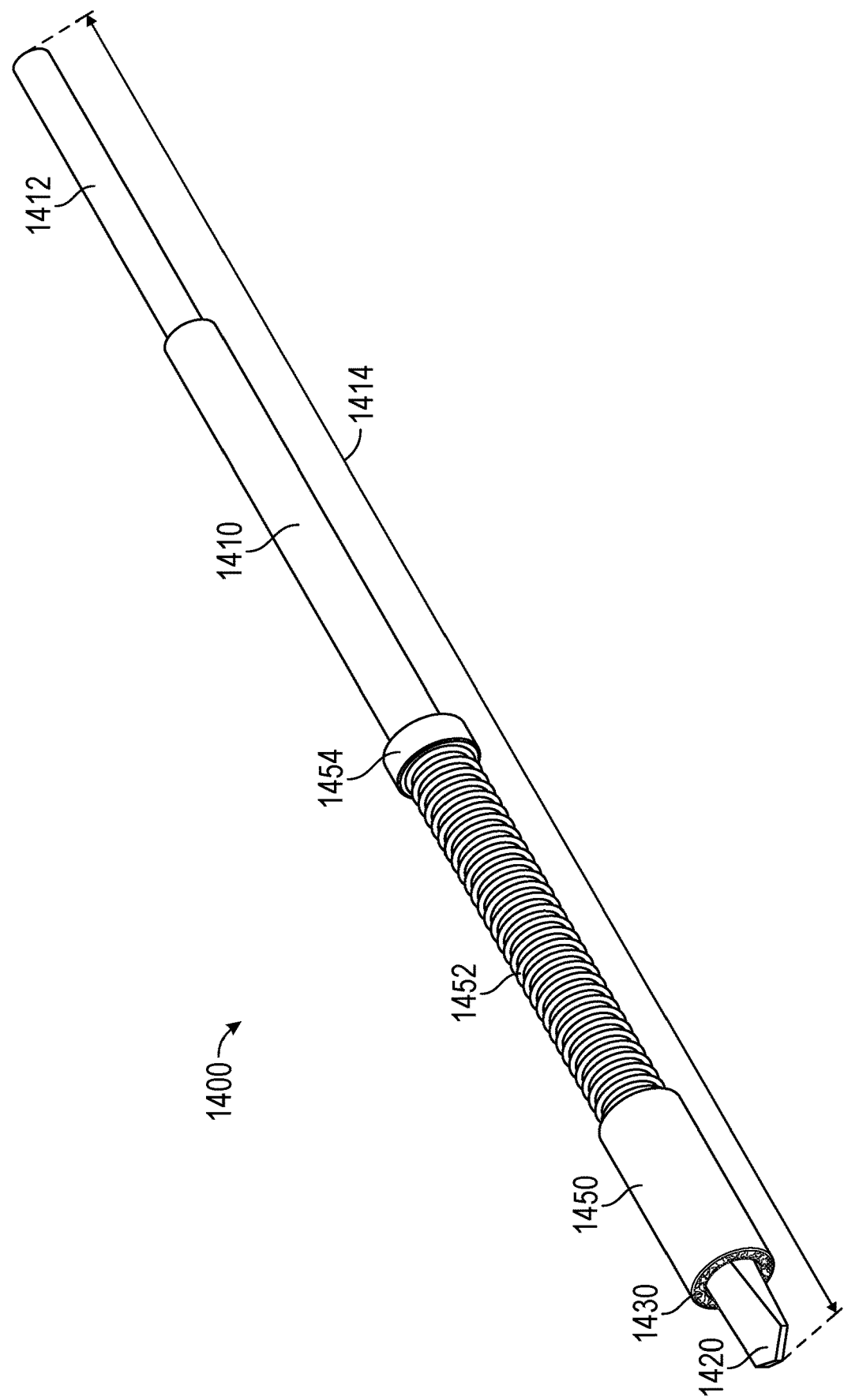
FIG. 14 illustrates an isometric view of an example device as per an aspect of an embodiment.

FIG. 14 illustrates an isometric view of an example medical device 1400 as per an aspect of an embodiment. The medical device 1400 may comprise an elongated member 1410. The medical device 1400 may comprise a hole forming surface 1420. The hole forming surface 1420 may comprise a first material. The medical device 1400 may comprise an open cell element 1430. The open cell element 1430 may comprise at least one second material. The open cell element 1430 may comprise a sleeve 1450. The sleeve 1450 may be configured to slide along a portion of the elongated member 1410. The sleeve 1450 may be employed, for example, to mark a top surface surrounding a formed hole. The top surface surrounding the formed hole may be marked through employment of a biocompatible substance at least partially housed in the open cell element 1430. The medical device 1400 may comprise a compression spring 1452. The compression spring 1452 may be employed to apply pressure to the sleeve 1450. The medical device 1400 may be configured to mark the top surface surrounding formed holes of a plurality of depths. The medical device 1400 may comprise a spring stop collar 1454. The spring stop collar 1454 may be fixed to the elongated member 1410. The position of the spring stop collar 1454 along the elongated member 1410 may be adjustable. The medical device 1400 may comprise a shank 1412. The medical device 1400 may comprise an overall length 1414.

Figure 15:
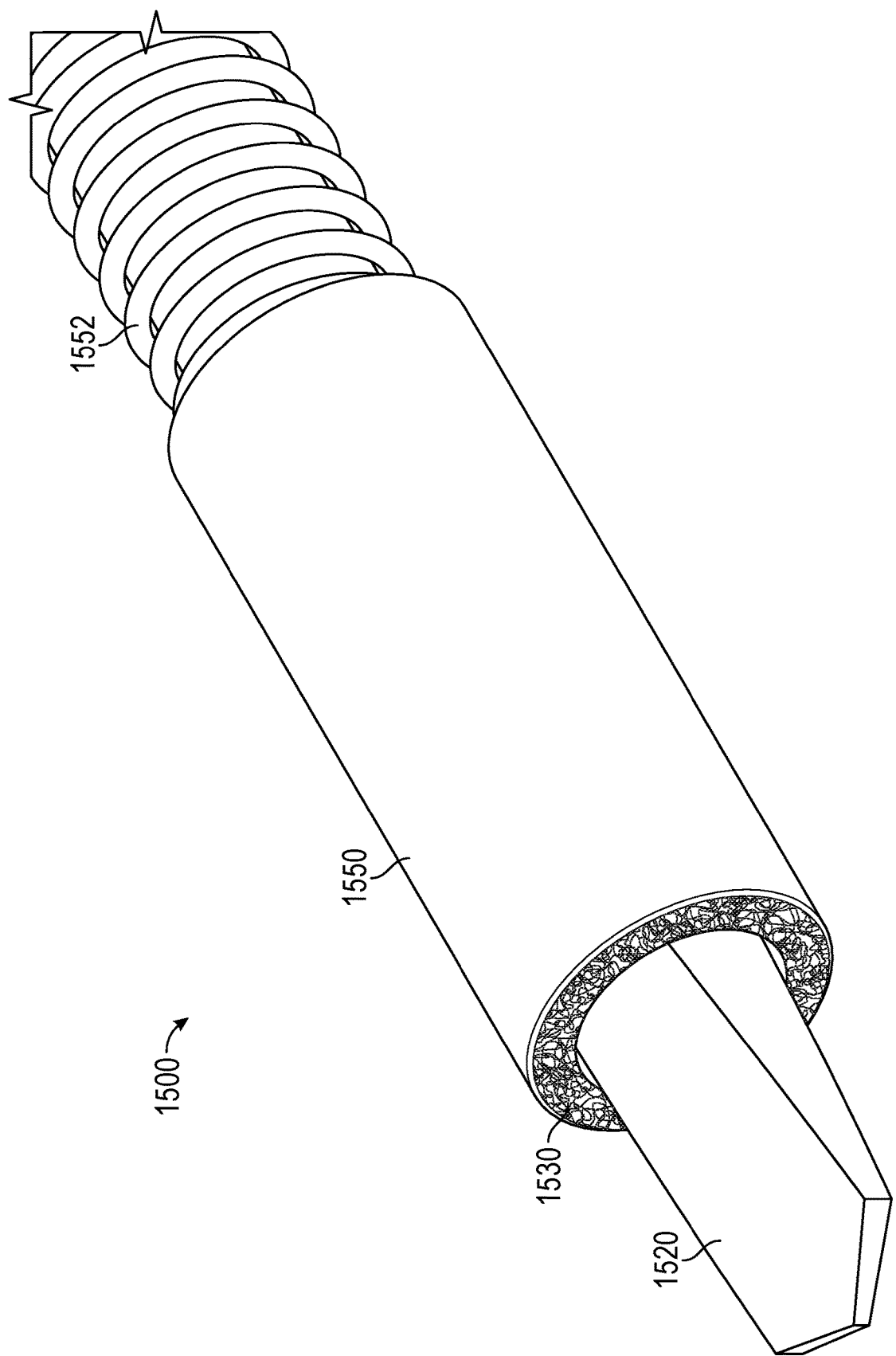
FIG. 15 illustrates an isometric view of a portion of an example device as per an aspect of an embodiment.

FIG. 15 illustrates an isometric view of a portion of an example medical device 1500 as per an aspect of an embodiment. The medical device 1500 may comprise an elongated member. The medical device 1500 may comprise a hole forming surface 1520. The hole forming surface 1520 may comprise a first material. The medical device 1500 may comprise an open cell element 1530. The open cell element 1530 may comprise at least one second material. The open cell element 1530 may comprise a sleeve 1550. The sleeve 1550 may be configured to slide along a portion of the elongated member. The sleeve 1550 and/or the open cell element 1530 may be employed, for example, to mark a top surface surrounding a formed hole. The top surface surrounding the formed hole may be marked through employment of a biocompatible substance at least partially housed in the open cell element 1530. The medical device 1500 may comprise a compression spring 1552. The compression spring 1552 may be employed to apply pressure to the sleeve 1550. The medical device 1500 may be configured to mark the top surface surrounding formed holes of a plurality of depths. The compression spring 1552 may have an extended position (as shown).

Figure 16:
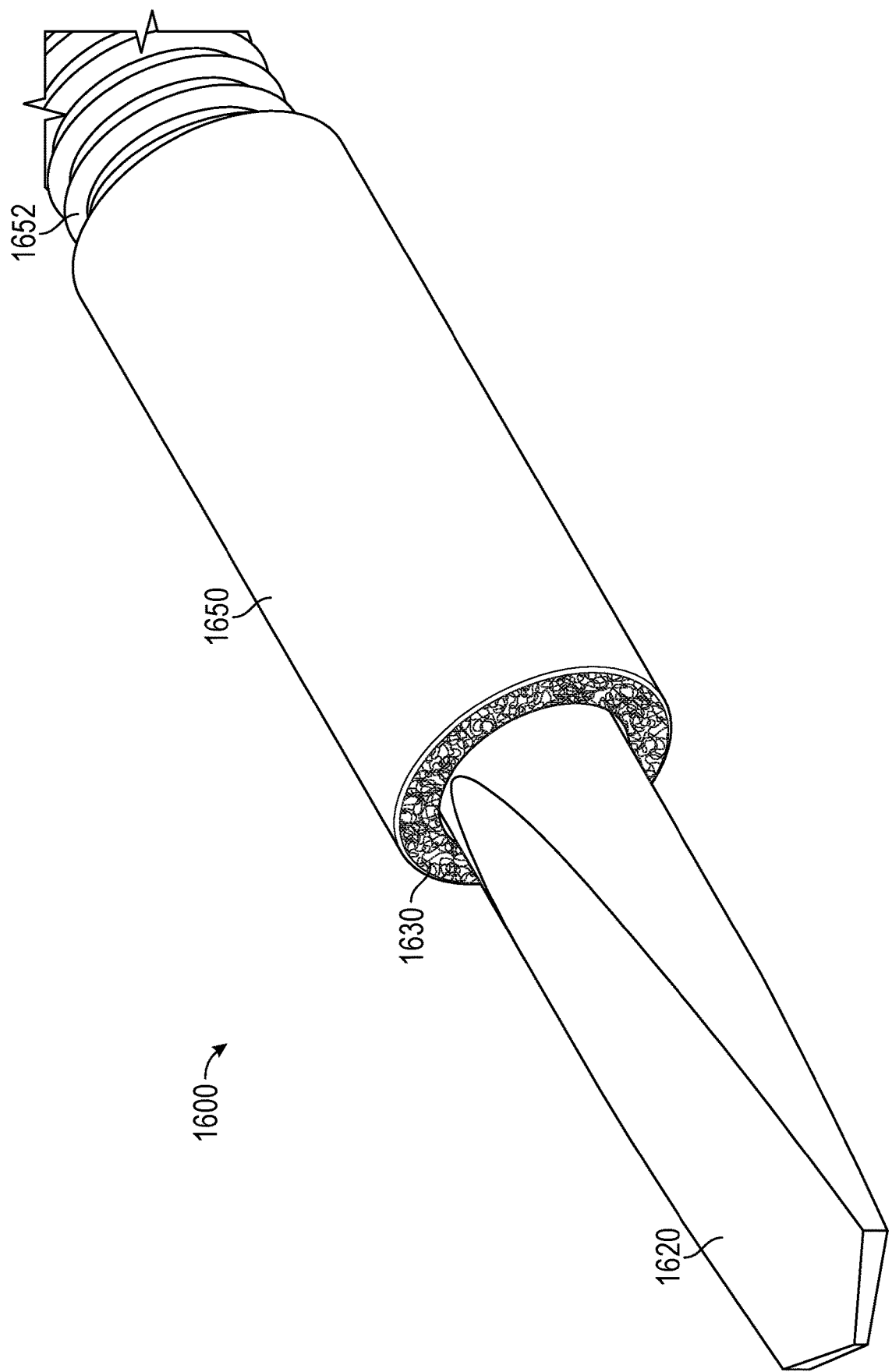
FIG. 16 illustrates an isometric view of a portion of an example device as per an aspect of an embodiment.

FIG. 16 illustrates an isometric view of a portion of an example medical device 1600 as per an aspect of an embodiment. The medical device 1600 may comprise an elongated member. The medical device 1600 may comprise a hole forming surface 1620. The hole forming surface 1620 may comprise a first material. The medical device 1600 may comprise an open cell element 1630. The open cell element 1630 may comprise at least one second material. The open cell element 1630 may comprise a sleeve 1650. The sleeve 1650 may be configured to slide along a portion of the elongated member. The sleeve 1650 may be employed to mark a top surface surrounding a formed hole. The top surface surrounding the formed hole may be marked through employment of a biocompatible substance at least partially housed in the open cell element 1630. The medical device 1600 may comprise a compression spring 1652. The compression spring 1652 may be employed to apply pressure to the sleeve 1650. The medical device 1600 may be configured to mark the top surface surrounding formed holes of a plurality of depths. The compression spring 1652 may have a compressed position (as shown).

According to an embodiment, a medical device may comprise a plurality of open cell elements. Each of the plurality of open cell elements may be in physical communication with the elongated member. Each of the plurality of open cell elements may be configured to house at least a portion of a biocompatible substance. The at least a portion of the biocompatible substance may be applied and at least partially dried, set, infused, combinations thereof, and/or the like by a manufacturer. The at least a portion of the biocompatible substance may be applied and at least partially dried, set, infused, combinations thereof, and/or the like by a user prior to use. Dried portions of the biocompatible substance may rehydrate when inserted into a physiological environment.

According to an embodiment, each of a plurality of open cell elements may comprise a second material. A first of the plurality of open cell elements may comprise the second material. A second of the plurality of open cell elements may comprise a third material. The third material may comprise surgical stainless steel. The third material may comprise a titanium alloy, a stainless steel alloy, a cobalt-chromium alloy, carbon fiber, a polymer, a ceramic, combinations thereof, and/or the like. The third material may comprise porous stainless steel. A porosity may be inherent to the third material. The porosity may be created using a secondary process (e.g. sintering). The first of the plurality of open cell elements may comprise a second porosity. The second of the plurality of open cell elements may comprise the second porosity. The second of the plurality of open cell elements may comprise a third porosity. The second and/or third porosity may be based on a specific biocompatible substance.

According to an embodiment, each of a plurality of open cell elements may be configured to release at least some of a biocompatible substance upon entrance into a physiological environment. Each of the plurality of open cell elements may be configured to accelerate the release of the biocompatible substance with rotation of an elongated member. Each of the plurality of open cell elements may be configured to directionalize the release of the biocompatible substance with rotation of the elongated member. Directionalization may be based on the structure of open cells in the open cell element and/or the orientation of the open cells in the open cell element. For example, a first of the plurality of open cell elements may be configured to directionalize the release of the biocompatible substance in a first direction. A second of the plurality of open cell elements may be configured to directionalize the release of the biocompatible substance in a second direction.

Figure 17:
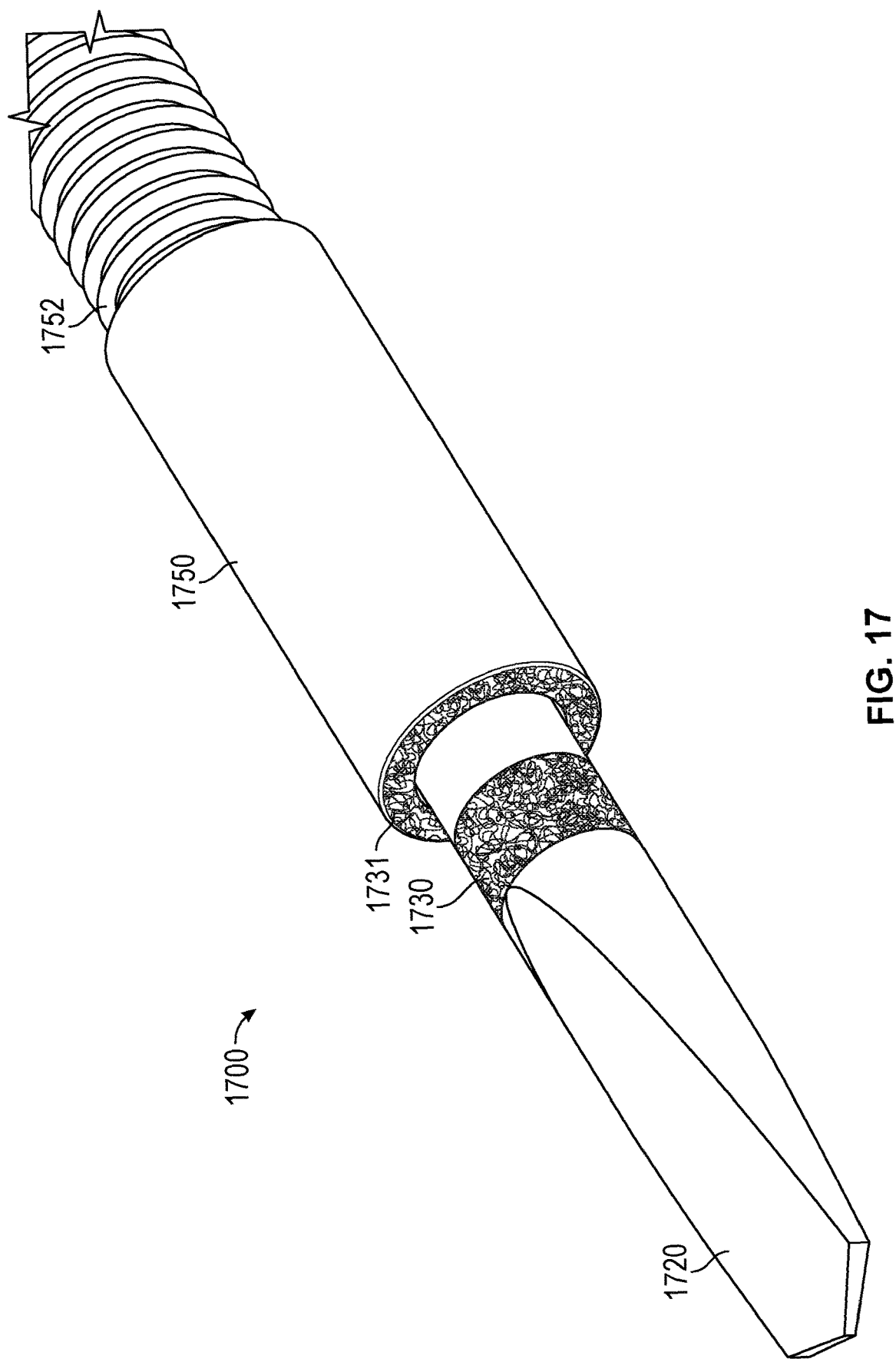
FIG. 17 illustrates an isometric view of a portion of an example device as per an aspect of an embodiment.

FIG. 17 illustrates an isometric view of a portion of an example medical device 1700 as per an aspect of an embodiment. The medical device 1700 may comprise an elongated member. The medical device 1700 may comprise a hole forming surface 1720. The hole forming surface 1720 may comprise a first material. The medical device 1700 may comprise a first open cell element 1730. The first open cell element 1730 may be configured to mark at least a portion of an interior surface of a hole formed by the hole forming surface 1720. The at least a portion of the interior surface of the hole may be marked through employment of a biocompatible substance at least partially housed in the open cell element 1730. The medical device 1700 may comprise a second open cell element 1731. The second open cell element 1731 may comprise the at least one second material. The second open cell element 1731 may comprise a sleeve 1750. The sleeve 1750 may be configured to slide along a portion of the elongated member. The sleeve 1750 may be employed to mark a top surface surrounding the hole formed by the hole forming surface 1720. The top surface surrounding the hole may be marked through employment of a biocompatible substance at least partially housed in the open cell element 1731. The medical device 1700 may comprise a compression spring 1752. The compression spring 1752 may be employed to apply pressure to the sleeve 1750. The medical device 1700 may be configured to mark the interior surface and the top surface surrounding formed holes of a plurality of depths. The compression spring 1752 may have a compressed position (as shown).

Figure 18:
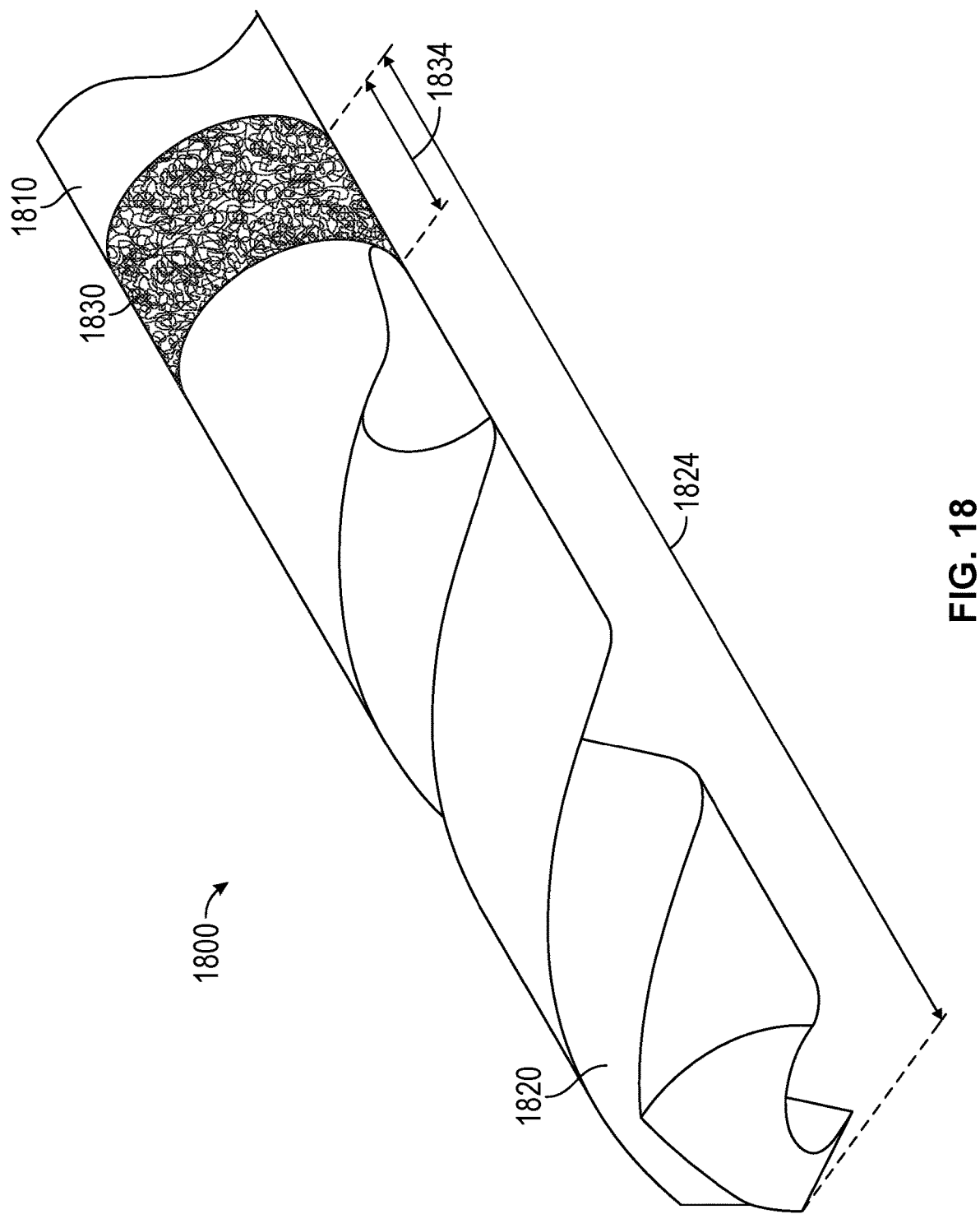
FIG. 18 illustrates an isometric view of a portion of an example device as per an aspect of an embodiment.

FIG. 18 illustrates an isometric view of a portion of an example medical device 1800 as per an aspect of an embodiment. The medical device 1800 may comprise an elongated member 1810. The medical device 1800 may comprise a hole forming surface 1820. The hole forming surface 1820 may comprise a first material. The medical device 1800 may comprise an open cell element 1830. The open cell element 1830 may comprise a marking depth 1834. The open cell element 1830 may comprise a second material. A distance from the tip of the hole forming surface 1820 to the end of the open cell element 1830 may comprise a target hole forming depth 1824.

According to an embodiment, a medical device may comprise a suction device configured to remove debris. The debris may comprise bone, cartilage, skin, muscle, fascia, tendon tissue, ligament tissue, adipose tissue, scar tissue, combinations thereof, and/or the like.

According to an embodiment, the fabrication of a medical device may comprise creating an open cell element by removing material from an elongated member. The elongated member may comprise a hole forming surface. For example, holes may be drilled perpendicular to the axis of the elongated member. For example, holes may be drilled at an angle from perpendicular to the axis of the elongated member. For example, holes may be drilled in a radial direction from the center of the elongated member. For example, holes may be drilled at an angle from a radial direction from the center of the elongated member. The fabrication of a medical device may comprise depositing a biocompatible substance in the open cell element. The open cell element may be structurally configured to release at least some of the biocompatible substance upon entrance into a physiological environment. The open cell element may be structurally configured to accelerate release of the biocompatible substance with rotation of the elongated member. The open cell element may be structurally configured to directionalize release of the biocompatible substance with rotation of the elongated member. The fabrication of a medical device may comprise causing at least some of the biocompatible substance to dry. At least some of the biocompatible substance may comprise liquid.

Figure 19:
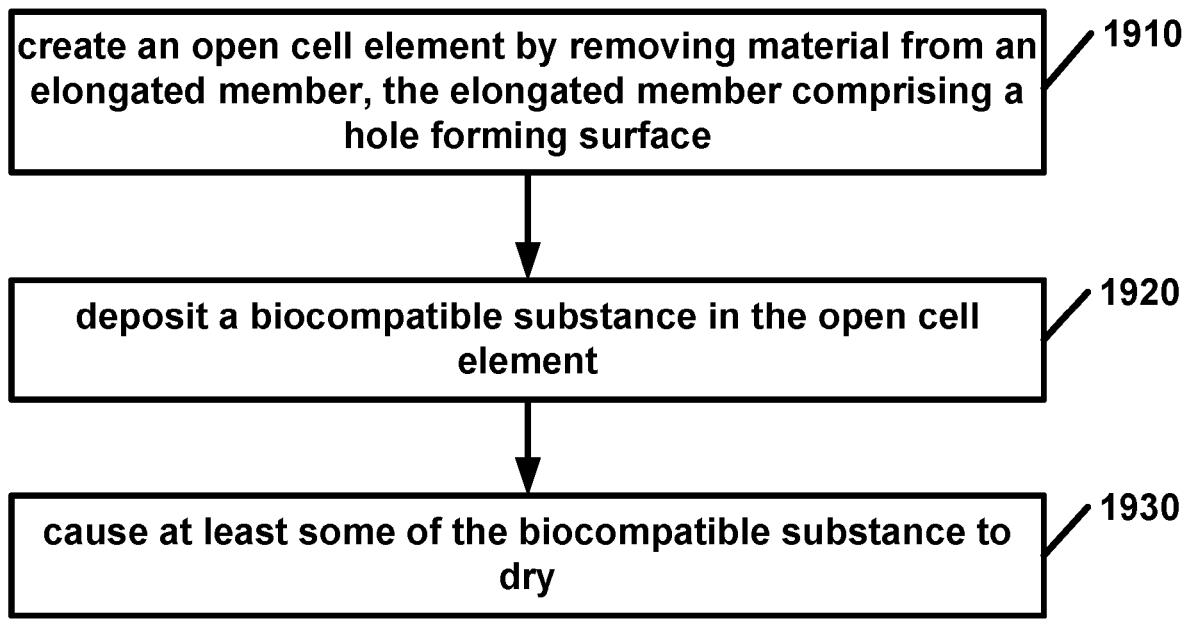
FIG. 19 is an example flow diagram of fabricating an example device as per an aspect of an embodiment.

FIG. 19 is an example flow diagram of fabricating an example medical device as per an aspect of an embodiment. An open cell element may be created at 1910. The open cell element may be created by removing material from an elongated member. The elongated member may comprise a hole forming surface. A biocompatible substance may be deposited in the open cell element at 1920. At least some of the biocompatible substance may be dried at 1930.

According to an embodiment, fabrication of a medical device may comprise attaching an open cell element to an elongated member. The open cell element may be structurally configured to release at least some of the biocompatible substance upon entrance into a physiological environment. The open cell element may be structurally configured to accelerate release of the biocompatible substance with rotation of the elongated member. The open cell element may be structurally configured to directionalize release of the biocompatible substance with rotation of the elongated member. The elongated member may comprise a hole forming surface. Attaching the open cell element to the elongated member may comprise fastening, laser welding, slipping the open cell element over the elongated member, wrapping, bonding, combinations thereof, and/or the like. The wrapping may, for example, employ tape, adhesive, heat shrink material, combinations thereof, and/or the like. The fabrication of a medical device may comprise depositing a biocompatible substance in the open cell element. At least some of the biocompatible substance may comprise liquid. The fabrication of a medical device may comprise causing at least some of the biocompatible substance to dry. The fabrication of a medical device may comprise creating a well in the elongated member. The fabrication of a medical device may comprise surrounding the well with the open cell element. The fabrication of a medical device may comprise attaching an open cell element retaining mechanism to the open cell element and the elongated member. The open cell element retaining mechanism may comprise a fastener, adhesive, heat shrink material, a bonding agent, combinations thereof, and/or the like.

Figure 20:
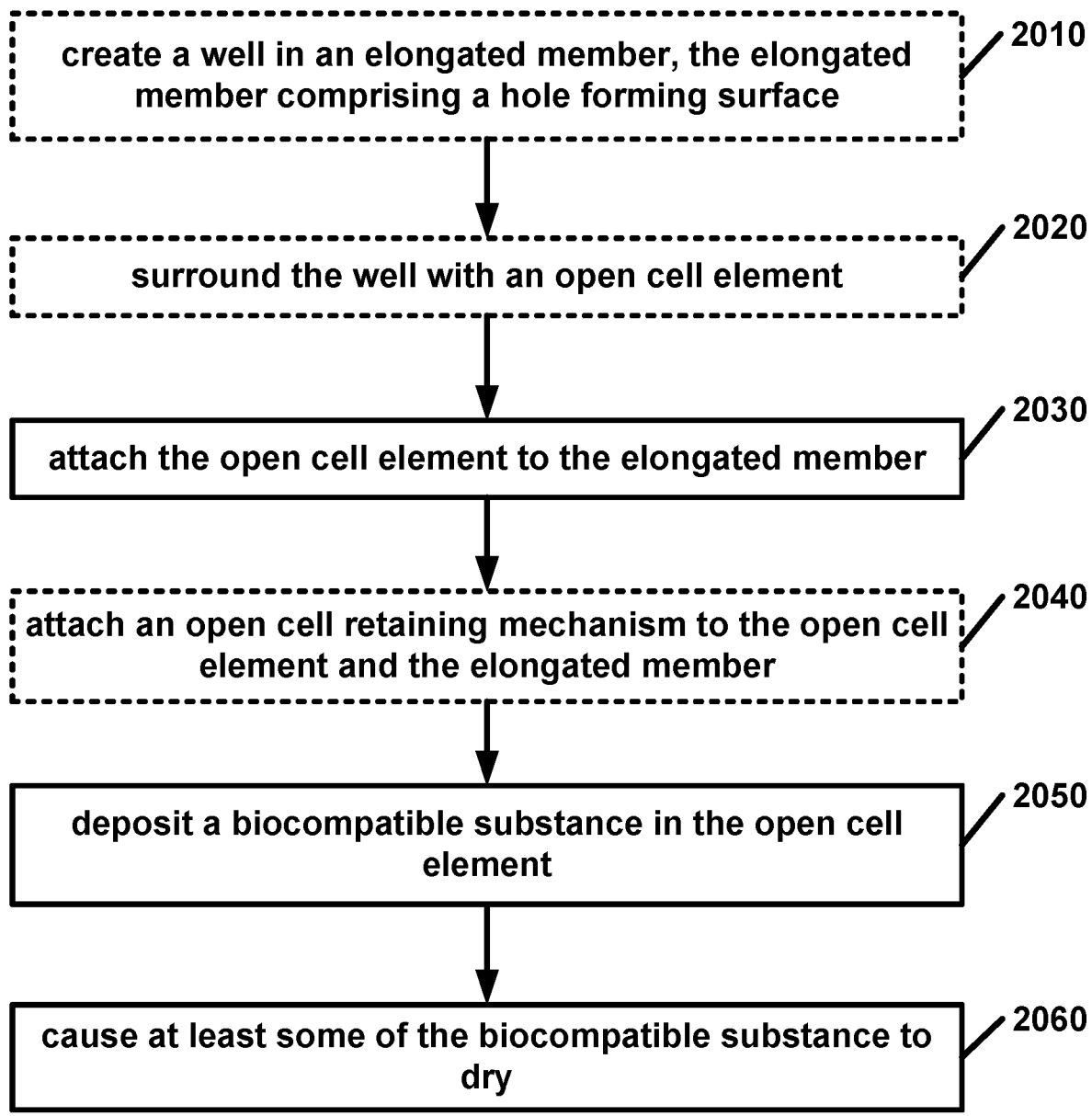
FIG. 20 is an example flow diagram of fabricating an example device as per an aspect of an embodiment.

FIG. 20 is an example flow diagram of fabricating an example medical device as per an aspect of an embodiment. A well may be created in an elongated member at 2010. The elongated member may comprise a hole forming surface. The well may be surrounded by an open cell element at 2020. The open cell element may be attached to the elongated member at 2030. An open cell retaining mechanism may be attached to the open cell element and the elongated member at 2040. A biocompatible substance may be deposited in the open cell element at 2050. At least some of the biocompatible substance may be dried at 2060.

According to an embodiment, a hole may be formed in bone, cartilage, skin, muscle, fascia, a tendon, a ligament, adipose tissue, scar tissue, combinations thereof, and/or the like. The hole may be formed employing a hole forming surface of an elongated member of a medical device. The medical device may be configured to be employed, for example, as a drill bit, a tap, a punch, a burr, a file, a cutter, a shaver, a cannula, a probe, a retractor, a stitching needle, combinations thereof, and/or the like. The hole may be marked with a biocompatible substance. The hole may be marked through employment of an open cell element. The open cell element may be in physical communication with the elongated member. The biocompatible substance may be stored in the open cell element prior to use. The biocompatible substance may be at least partially dried prior to use. The disclosed process may be employed, for example, as part of an arthroscopic and/or orthopedic surgery.

Figure 21:
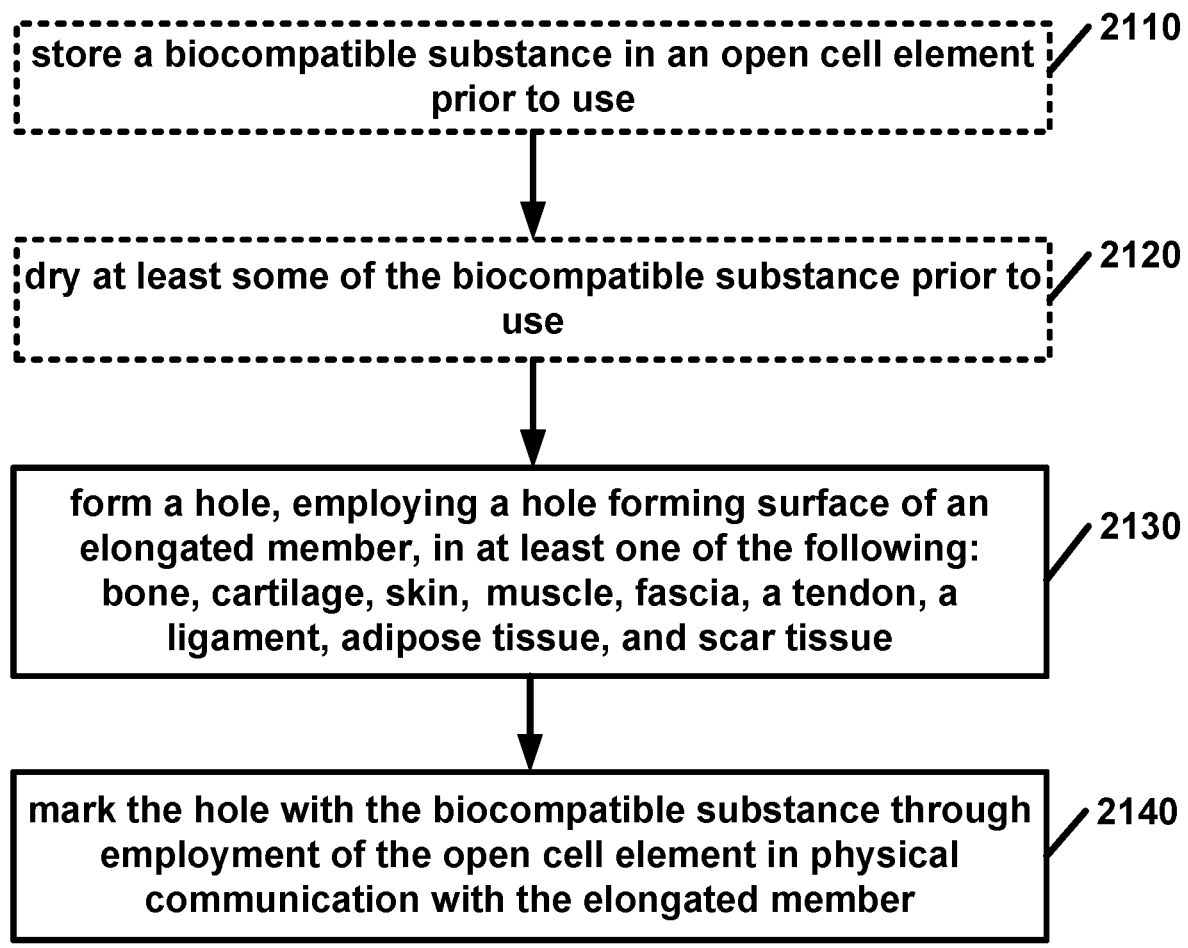
FIG. 21 is an example flow diagram of employing an example device as per an aspect of an embodiment.

FIG. 21 is an example flow diagram of employing an example medical device as per an aspect of an embodiment. A biocompatible substance may be stored in an open cell element at 2110. The biocompatible substance may be stored in the open cell element prior to use. At least some of the biocompatible substance may be dried at 2120. At least some of the biocompatible substance may be dried prior to use. A hole may be formed at 2130. The hole may be formed employing a hole forming surface of an elongated member. The hole may be formed in at least one of the following: bone, cartilage, skin, muscle, fascia, a tendon, a ligament, adipose tissue, and scar tissue. The hole may be marked at 2140. The hole may be marked with the biocompatible substance. The hole may be marked through employment of the open cell element. The open cell element may be in physical communication with the elongated member.

According to an embodiment, a hole may be enlarged in bone, cartilage, skin, muscle, fascia, a tendon, a ligament, adipose tissue, scar tissue, combinations thereof, and/or the like. The hole may be enlarged employing a hole forming surface of an elongated member of a medical device. The medical device may be configured to be employed, for example, as a drill bit, a tap, a punch, a burr, a file, a cutter, a shaver, a cannula, a probe, a retractor, a stitching needle, combinations thereof, and/or the like. The hole may be marked with a biocompatible substance. The hole may be marked through employment of an open cell element. The open cell element may be in physical communication with the elongated member. The biocompatible substance may be stored in the open cell element prior to use. The biocompatible substance may be at least partially dried prior to use. The disclosed process may be employed, for example, as part of an arthroscopic and/or orthopedic surgery.

Figure 22:
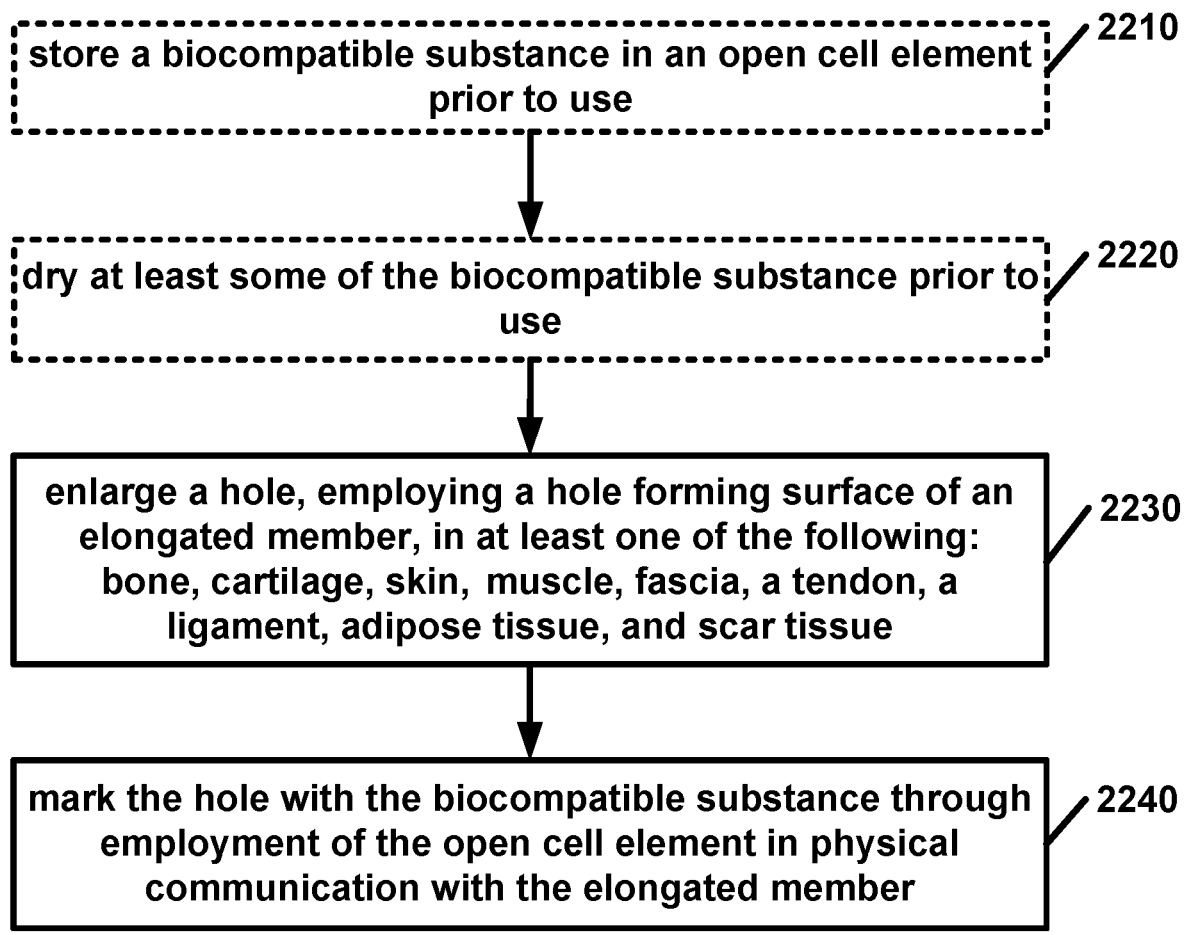
FIG. 22 is an example flow diagram of employing an example device as per an aspect of an embodiment.

FIG. 22 is an example flow diagram of employing an example medical device as per an aspect of an embodiment. A biocompatible substance may be stored in an open cell element at 2210. The biocompatible substance may be stored in the open cell element prior to use. At least some of the biocompatible substance may be dried at 2220. At least some of the biocompatible substance may be dried prior to use. A hole may be enlarged at 2230. The hole may be enlarged employing a hole forming surface of an elongated member. The hole may be enlarged in at least one of the following: bone, cartilage, skin, muscle, fascia, a tendon, a ligament, adipose tissue, and scar tissue. The hole may be marked at 2240. The hole may be marked with the biocompatible substance. The hole may be marked through employment of the open cell element. The open cell element may be in physical communication with the elongated member.

According to an embodiment, a section of bone, cartilage, skin, muscle, fascia, a tendon, a ligament, adipose tissue, scar tissue, combinations thereof, and/or the like may be trimmed. The section may be trimmed employing a cutting surface of an elongated member of a medical device. The medical device may be configured to be employed, for example, as a burr, a file, a cutter, a shaver, a retractor, combinations thereof, and/or the like. The tissue surrounding the section may be marked with a biocompatible substance. The tissue surrounding the section may be marked through employment of an open cell element. The open cell element may be in physical communication with the elongated member. The biocompatible substance may be stored in the open cell element prior to use. At least some of the biocompatible substance may be dried prior to use. The disclosed process may be employed, for example, as part of an arthroscopic and/or orthopedic surgery.

Figure 23:
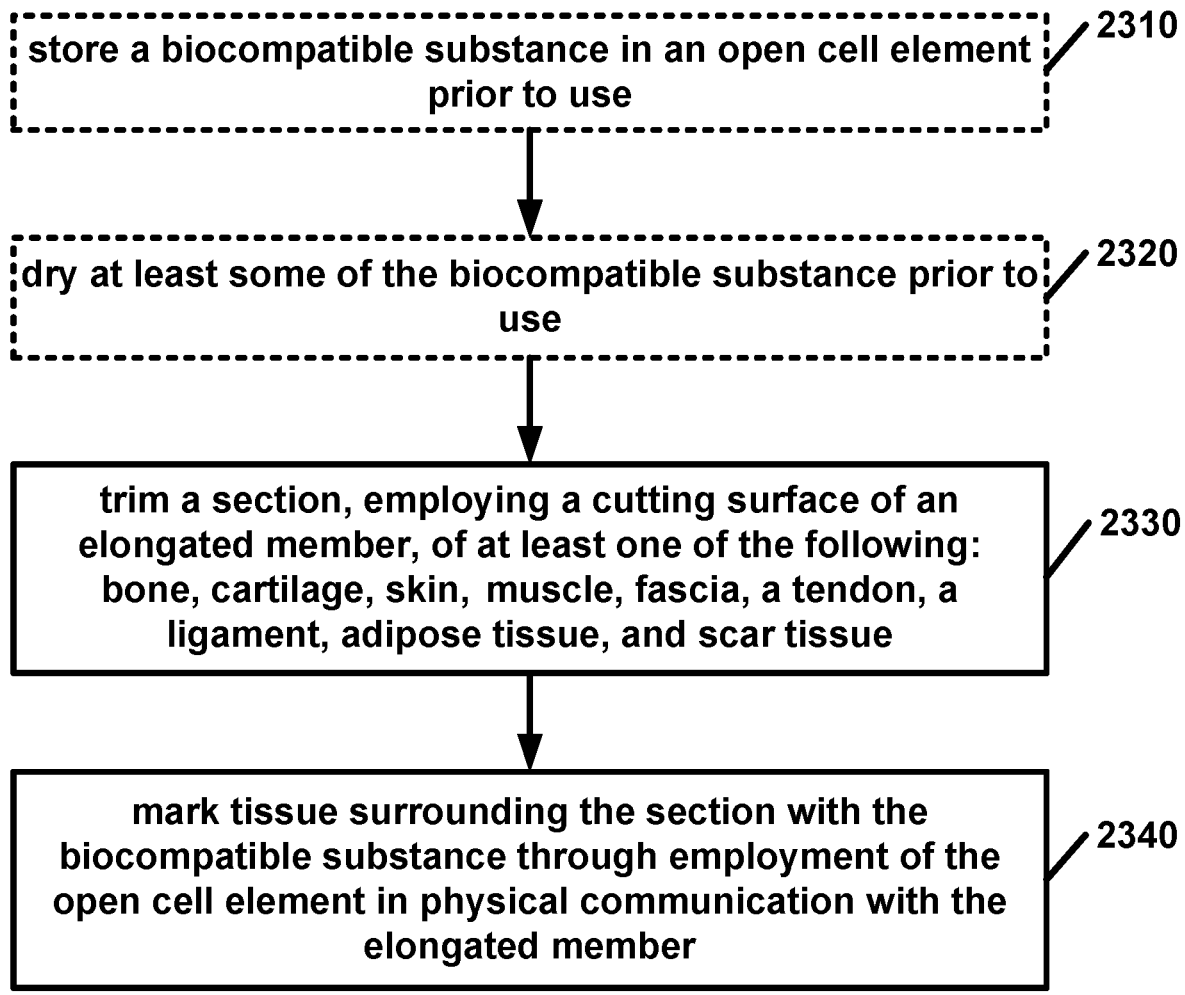
FIG. 23 is an example flow diagram of employing an example device as per an aspect of an embodiment.

FIG. 23 is an example flow diagram of employing an example medical device as per an aspect of an embodiment. A biocompatible substance may be stored in an open cell element at 2310. The biocompatible substance may be stored in the open cell element prior to use. At least some of the biocompatible substance may be dried at 2320. At least some of the biocompatible substance may be dried prior to use. A section may be trimmed at 2330. The section may be trimmed employing a cutting surface of an elongated member. The section may be trimmed from at least one of the following: bone, cartilage, skin, muscle, fascia, a tendon, a ligament, adipose tissue, and scar tissue. Tissue surrounding the section may be marked at 2340. The tissue surrounding the section may be marked with the biocompatible substance. The tissue surrounding the section may be marked through employment of the open cell element. The open cell element may be in physical communication with the elongated member.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

In this specification, "a" and "an" and similar phrases are to be interpreted as "at least one" and "one or more." References to "a", "an", and "one" are not to be interpreted as "only one". In this specification, the term "may" is to be interpreted as "may, for example." In other words, the term "may" is indicative that the phrase following the term "may" is an example of one of a multitude of suitable possibilities that may, or may not, be employed to one or more of the various embodiments. In this specification, the phrase "based on" is indicative that the phrase following the term "based on" is an example of one of a multitude of suitable possibilities that may, or may not, be employed to one or more of the various embodiments. References to "an" embodiment in this disclosure are not necessarily to the same embodiment.

While various embodiments have been described above, it should be understood that they have been presented by way of example, and not limitation. It will be apparent to persons skilled in the relevant art(s) that various changes in form and detail can be made therein without departing from the spirit and scope. In fact, after reading the above description, it will be apparent to one skilled in the relevant art(s) how to implement alternative embodiments. Thus, the present embodiments should not be limited by any of the above described exemplary embodiments. For example, additional embodiments may exist for non-medical applications, such as delivering a substance when working a material. Examples of substances may comprise glue, lubricant, filler, ink, combinations thereof, and/or the like. Some glues may behave based on their environment (for example, solid when exposed to air and liquid when exposed to heat and/or moisture). For example, if one is machining a material (such as plastic, metal, wood, and/or the like), the substance may become obscured, worn, difficult to view, and/or otherwise prevented from performing an intended function.

In this specification, various embodiments are disclosed. Limitations, features, and/or elements from the disclosed example embodiments may be combined to create further embodiments within the scope of the disclosure.

In addition, it should be understood that any figures that highlight any functionality and/or advantages, are presented for example purposes only. The disclosed structure is sufficiently flexible and configurable, such that it may be utilized in ways other than that shown. For example, the steps listed in any flowchart may be re-ordered or only optionally used in some embodiments.

Furthermore, many features presented above are described as being optional through the use of "may" or the use of parentheses. For the sake of brevity and legibility, the present disclosure does not explicitly recite each and every permutation that may be obtained by choosing from the set of optional features. However, the present disclosure is to be interpreted as explicitly disclosing all such permutations. For example, an apparatus described as having three optional features may be embodied in seven different ways, namely with just one of the three possible features, with any two of the three possible features or with all three of the three possible features.

Further, the purpose of the Abstract of the Disclosure is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract of the Disclosure is not intended to be limiting as to the scope in any way.

Finally, it is the applicant's intent that only claims that include the express language "means for" or "step for" be interpreted under 35 U.S.C. 112. Claims that do not expressly include the phrase "means for" or "step for" are not to be interpreted under 35 U.S.C. 112.

What is claimed is:

1. A medical device comprising:
   a) a non-cannulated elongated member;
   b) a hole forming surface along a portion of the non-cannulated elongated member; and
   c) an open cell element in physical communication with the non-cannulated elongated member, the open cell element disposed between both ends of the elongated member, the open cell element configured to:
   i) house at least a first portion of a biocompatible substance;
   ii) release at least some of the biocompatible substance upon entrance of the open cell element into a physiological environment; and
   iii) accelerate release of the biocompatible substance with rotation of the non-cannulated elongated member.

2. The medical device according to claim 1, wherein the medical device is configured to be employed as one of the following:
   a) a drill bit;
   b) a tap;
   c) a punch;
   d) a burr;
   e) a file;
   f) a cutter;
   g) a shaver;
   h) a probe;
   i) a retractor; and
   j) a stitching needle.

3. The medical device according to claim 1, wherein the hole forming surface comprises a first material, and the open cell element comprises a second material.

4. The medical device according to claim 3, wherein at least one of the first material and the second material comprises surgical stainless steel.

5. The medical device according to claim 3, wherein at least one of the first material and the second material comprises porous stainless steel.

6. The medical device according to claim 1, wherein the hole forming surface comprises a first porosity, and the open cell element comprises a second porosity.

7. The medical device according to claim 1, wherein the non-cannulated elongated member comprises a well, the well surrounded by the open cell element and configured to house at least a second portion of the biocompatible substance.

8. The medical device according to claim 1, wherein at least some of the biocompatible substance is dry.

9. The medical device according to claim 1, wherein the open cell element is further configured to directionalize release of the biocompatible substance with rotation of the non-cannulated elongated member.

10. The medical device according to claim 1, wherein the open cell element is incorporated with the non-cannulated elongated member, the open cell element comprising at least one of:
   a) a ring;
   b) a sleeve;
   c) a collar; and
   d) a segment of the non-cannulated elongated member.

11. The medical device according to claim 1, wherein the open cell element is fastened to the non-cannulated elongated member, the open cell element comprising at least one of:
   a) a ring;
   b) a sleeve;
   c) a collar; and
   d) an additional segment.

12. The medical device according to claim 1, wherein the open cell element is configured to slide along at least a portion of the non-cannulated elongated member.

13. The medical device according to claim 1, wherein the biocompatible substance comprises at least one of the following:
   a) an ink;
   b) a dye;
   c) a stain;
   d) an analgesic agent;
   e) a medication;
   f) a coagulant;
   g) patient blood;
   h) stem cells;
   i) an anti-inflammatory agent;
   j) a hemostatic agent;
   k) an antibacterial agent; and
   l) a bio-stimulatory agent.

14. The medical device according to claim 1, wherein at least some of the biocompatible substance comprises liquid.

15. The medical device according to claim 1, the medical device configured to:
   a) form a hole in at least one of the following:
      i) bone;
      ii) cartilage;
      iii) skin;
      iv) muscle;
      v) fascia;
      vi) a tendon;
      vii) a ligament;
      viii) adipose tissue; and
      ix) scar tissue; and
   b) deliver the biocompatible substance to the hole.

16. The medical device according to claim 1, the medical device configured to:
   a) enlarge a hole in at least one of the following:
      i) bone;
      ii) cartilage;
      iii) skin;
      iv) muscle;
      v) fascia;
      vi) a tendon;
      vii) a ligament;
      viii) adipose tissue; and
      ix) scar tissue; and
   b) deliver the biocompatible substance to the hole.

17. The medical device according to claim 1, the medical device configured to:
   a) cut a section of at least one of the following:
      i) bone;
      ii) cartilage;
      iii) skin;
      iv) muscle;
      v) fascia;
      vi) a tendon;
      vii) a ligament;
      viii) adipose tissue; and
      ix) scar tissue; and
   b) deliver the biocompatible substance to the section.

18. The medical device according to claim 1, the medical device configured to:
   a) shave a section of at least one of the following:
      i) bone;
      ii) cartilage;
      iii) skin;
      iv) muscle;
      v) fascia;
      vi) a tendon;
      vii) a ligament;
      viii) adipose tissue; and
      ix) scar tissue; and
   b) deliver the biocompatible substance to the section.

19. The medical device according to claim 1, further comprising a suction device configured to remove debris comprising at least one of the following:
   a) bone;
   b) cartilage;
   c) skin;
   d) muscle;
   e) fascia;
   f) tendon tissue;
   g) ligament tissue;
   h) adipose tissue; and
   i) scar tissue.

* * * * *